US006218521B1

(12) United States Patent
Obata

(10) Patent No.: US 6,218,521 B1
(45) Date of Patent: Apr. 17, 2001

(54) ISOLATED NUCLEIC ACID MOLECULES ASSOCIATED WITH GASTRIC CANCER AND METHODS FOR DIAGNOSING AND TREATING GASTRIC CANCER

(75) Inventor: Yuichi Obata, Nagoya (JP)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 08/896,164

(22) Filed: Jul. 17, 1997

(51) Int. Cl.[7] .......................... C07H 21/02; C07H 21/04; C12N 15/00; C12N 15/09
(52) U.S. Cl. .................... 536/23.1; 536/23.5; 435/320.1; 435/252.3; 435/325
(58) Field of Search .................... 536/23.1, 23.5; 435/325, 320.1, 252.3

(56) References Cited

U.S. PATENT DOCUMENTS 5,698,396   12/1997   Pfreundschuh .

OTHER PUBLICATIONS dePlaen et al., *Proc. Natl. Sci. USA* 85:2275, 1988.
Mandelboim, et al., *Nature* 369:69 1994.
van der Bruggen et al., *Science* 254:1643–1647, 1991.
Brichard et al., *J. Exp. Med.* 178:489–495, 1993.
Coulie et al., *J. Exp. Med.* 180:35–42, 1994.
Kawakami et al., *Proc. Natl. Acad. Sci, USA* 91:3515–3519, 1994.
Oettgen et al., *Immunol. Allerg. Clin. North. Am*, 10:607–637, 1990.
Sahin et al., *Proc. Natl. Acad. Sci. USA* 92:11810–11913, 1995.
Crew et al., *EMBO J* 144:2333–2340, 1995.
Chen et al., *Proc. Natl. Acad. Sci. USA* 94:1914 (1997).
Türeci et al., *Cancer Research* 56:4766–4772, 1996.
1994–1995 Promega Catalog, p. 167.*
Genebank Accession No: N25768 (Dec. 29, 1995).*
Genebank Accession No: N28891 (Jan. 4, 1996).*
Genebank Accession No: W74607 (Jun. 20, 1996).*
Genebank Accession No: AA 004205 (Jul. 23, 1996).*
Genebank Accession No: AA 007407 (Jul. 25, 1996).*
Genebank Accession No: T24694 (Oct. 9, 1996).*
Genebank Accession No: W45570 (Oct. 10, 1996).*
Genebank Accession No: W92012 (Feb. 2, 1997).*
Genebank Accession No: AA114952 (May. 11, 1997).*
Genebank Accession No: AA431793 (May 22, 1997).*

* cited by examiner

*Primary Examiner*—Yvonne Eyler
*Assistant Examiner*—Jennifer Nichols
(74) *Attorney, Agent, or Firm*—Wolf, Greenfield & Sacks, P.C.

(57) ABSTRACT

Various molecules associated with disorders such as gastric cancer are disclosed. The invention also discloses diagnostic and therapeutic methods based upon these molecules.

19 Claims, No Drawings

SEQUENCE LISTING (1) GENERAL INFORMATION:

(iii) NUMBER OF SEQUENCES: 87

(2) INFORMATION FOR SEQ ID NO: 1:

(i) SEQUENCE CHARACTERISTICS:
        (A) LENGTH: 707 base pairs
        (B) TYPE: nucleic acid
        (C) STRANDEDNESS: double
        (D) TOPOLOGY: linear (xi) SEQUENCE DESCRIPTION: SEQ ID NO: 1:

```
AGATGGCGCC TGTTGTGACA GGGAAATTTG GTGAGCGGCC TCCACCTAAA CGACTTACTA        60

GGGAAGCTAT GCGAAATTAT TTAAAAGAGC GAGGGGATCA AACAGTNCTT ATTCTTCATG       120

CAAAAGTTGC ACAGAAGTCA TATGGAAATG AAANAAGGTT TTTTTGCCCA CCTCCTTGTG       180

TATATCTTAT GGGCANTGGA TGGAAGAAAA AAAANGAACA AATGGAACGC GATGGTTGTT       240

CTGAACAAAA GTCTCAACCG TGTGCATTTA TTGGGATAGG AAATAGTGAC CAAAAAATGC       300

AGCAGCTANA CTTGGAAGGA AAGAACTATT GCACAGCCAA AACATTGTAT ATATCTGACT       360

CAGACAAGCG AAAGCACTTC ATGTTGTCTG TAAAGATGTT CTATGGCAAC AGTGATGACA       420

TTGGTGTGTT CCTCAGCAAG CGAATAAAAG TCNTCTCCAA ACCTTCCAAA AAGAACAGTC       480

ATTGAAAAAT GCTGACTTAT GCATTGCCTC ANGAACAAAG GTGGCTCTGT TTAATCGACT       540

ACNATCCCAN ACAGTTAGTA CCAGATACTT GCATGTTANA AGGAGGTNAT TTTCATGCCA       600

GTTCACAGCN GTGGGAGCC TTTTTTATTC ANCTCTTGGA TGATGATGAN TCCNAAGGAG       660

AAGAATTCAC NGTCCGAGAT GGCTACATCC ATTATGGACA AACAGTC                    707
```

(2) INFORMATION FOR SEQ ID NO: 2:

(i) SEQUENCE CHARACTERISTICS:
        (A) LENGTH: 551 base pairs
        (B) TYPE: nucleic acid
        (C) STRANDEDNESS: double
        (D) TOPOLOGY: linear (xi) SEQUENCE DESCRIPTION: SEQ ID NO: 2:

```
ACTGTGGCTT CTGCATTTCA AATCAGCACT TGCAGGGAGA CAACGGGGTT TTTGAATAGT        60

ATCACCTGGT ATGAAAAGTT TTCCCAAGAA ACCACAAACG ATTGTTCATT TTTTCTCCTT       120

TTTTGTTAAC TTTTTGCCAC ACTCAAGTCA GTTTAAGTCC TAGCAAAAAG ACGGTAGTTA       180

GGATACCACT GTGGCTGTAN ATGATGTGAC ACTGGTTGAA TTTGTGCTGG CGTTTGTGTA       240

ACTTCCCTCG CTGTTTGTGT TTGATTCGTT AGGGGGCACC TGGCTTGAAT TGGCTCGAAG       300

GATTGCTCCT GCTGCACTGC AATGTGGCCG CGGCCCTGGT TCTGGTGTGT ANGTAAAGGT       360
```

```
AAGGCTGGTG GAATAAATGA TTCCACCATT TCGGACCAAA GTTACTGGAA CCTGGACTGG      420

TTGCCGGACC CATCTCCAAC CTTCTCGGAA TGCANAAATG TCTGGGACGA CACAGAACAT      480

ACCTCTCCAC ACCTGTACAT AATTTCAGCT TCTACATCCC CAAACCACAC TCGTAAATTT      540

GGANTNAAAA T                                                          551
```

(2) INFORMATION FOR SEQ ID NO: 3:

(i) SEQUENCE CHARACTERISTICS:
        (A) LENGTH: 478 base pairs
        (B) TYPE: nucleic acid
        (C) STRANDEDNESS: double
        (D) TOPOLOGY: linear (xi) SEQUENCE DESCRIPTION: SEQ ID NO: 3:

```
ACTGTGGCTT CTGCATTTCA ATCAGCACT TGCAGGGANA CAACGGGGTT TTTGAATAGT       60

ATCACCTGGT ATGAAAAGTT TTCCCAAGAA ACCACAAACN ATTGTTCATT TTTTCTCCTT     120

TTTTGTTAAC TTTTNGCCAC ACTCAANTCA GTTTAAGTCC TAGCAAAAAN ACGGTAGTTA     180

GGATACCACT GTGGCTGTAA ATGATNTGAC ACTGGTTGAA TTTGTGCTGG CGTTTGTGTA     240

ACTTCCCTCG CTGTTTGTGT TTGATTCGTN AGGGGGCACC TGGCTTGAAT TGGCTCGAAG     300

GATTGCTCCT GCTGCACTGC AATGTGGCCG CGGGCCTGNT TCTTATNTGT TGTAAANGTN     360

AGGNTGGTGG AATAAATGAT TCCATCATNT CGGANCGAAG TTGCTGGGAA CTGGGANNGG     420

TNGNCGGAAC CATCTCCGAC CNCCCGGAAA NGCAGAAGTG TTNGTGGNAG ACCGGAAC      478
```

(2) INFORMATION FOR SEQ ID NO: 4:

(i) SEQUENCE CHARACTERISTICS:
        (A) LENGTH: 707 base pairs
        (B) TYPE: nucleic acid
        (C) STRANDEDNESS: double
        (D) TOPOLOGY: linear (xi) SEQUENCE DESCRIPTION: SEQ ID NO: 4:

```
ACTGTGGCTT CTGCATTTCA ATCAGCACT TGCAGGGAGA CAACGGGGTT TTTGAATAGT       60

ATCACCTGGT ATGAAAAGTT TTCCCAANAA ACCACAAACG ATTGTTCATT TTTTCTCCTT     120

TTTTGTTAAC TTTTTGCCAC ACTCAANTCA GTTTAANTCC TANCAAAAAG ACGGTAGTTA     180

GGATACCACT GTGGCTGTAA ATGATGTGAC ACTGGTTGAA TTTGTGCTGG CGTTTGTGTA     240

ACTTCCCTCG CTGTTTGTGT TTGATTCGTT AGGGGGCACC TGGCTTGAAT TGGCTCGAAG     300

GATTGCTCCT GCTGCACTGC AATGTGGCCG CGGCCCTGGT TCTGGTGTGT AGGTAAAGGT     360

AAGGCTGGTG GAATAAATGA TTCCATCATT TCGGACCAAA GTTACTGGAA CCTGGACTGG     420

TTGCCGGACC CATCTCCAAC CTTCTCGGAA TGCAGAAATG TCTGGGACGA CACAGANCAT     480

ACTCTCTCCA CACCTGTACA TAGTTTCNGC TTCTACATCC CCAAACCACA CTCGTAAATT     540

TGGANTGAAA TTCTGTCCTG TAAGTTCAAG CATTNCTACG TCCCCACCCG CCATTTCAAC     600

TGAAAGGCTC TCTACCACAN GGNACAGGAA ATGACTGGGG CAAGGACAGG GCCCATTCCC     660

TCATTAAATG TNATACTCCG CCTTATCNGT CCTAAANGAA TGTNCAA                   707
```

(2) INFORMATION FOR SEQ ID NO: 5:

(i) SEQUENCE CHARACTERISTICS:
        (A) LENGTH: 541 base pairs
        (B) TYPE: nucleic acid
        (C) STRANDEDNESS: double
        (D) TOPOLOGY: linear (xi) SEQUENCE DESCRIPTION: SEQ ID NO: 5:

```
GGTAAACTTT TGGCCACNCN CAATTCANTT TAATTCCTAC CAAAAAAACG GTATTTAGNA      60
TNCCNCTGTG GCTGTAAATA ATTTAACNCT GGTTAAATTN NTNCTGGCTT TNGTNTANCT     120
CCCCCCCCTN TTNGTTTTTN ATCCNTTAGG GGGCACCTGN CTTNANTGGG CNCAAAGGAT     180
NGCCCCTGCT GCANTGCAAT TTGGCCNCGG CCCTGGTCCT GGTTTNTAGG TAAAGGTAAG     240
GCNGGTGNAA TAANTAATCC CACCATTNCG NACCAAATTT ACTGNAACCT GAACNGGTTG     300
CCGNACCCAN CNCCANCCTN CNCGAAATGC AAAANTTTCT GGNACAACNC AAACCNTACN     360
CNCNCCACCC CTNTNCNTAT TTNCAGCTNC TACNTCCCCA AACCACACNC NTAAATTNGN     420
ATTAAAATCC TNTCCTGTAA TTCCAAGCAT GGCTACTTCC CCACCGCCAT TCAACTNAAG     480
GCCCNCTACC ACAGGCNCAG NATTAANTGG GGCAAGGAAA GGGCCCATCC CCCCATAAAA     540
T                                                                    541
```

(2) INFORMATION FOR SEQ ID NO: 6:

(i) SEQUENCE CHARACTERISTICS:
        (A) LENGTH: 605 base pairs
        (B) TYPE: nucleic acid
        (C) STRANDEDNESS: double
        (D) TOPOLOGY: linear (xi) SEQUENCE DESCRIPTION: SEQ ID NO: 6:

```
ACTGTGGCTT CTGCATTTCA AATCAGCACT TGCAGGGANA CAACGGGGTT TTTGAATANT      60
ATCACCTGGT ATGAAAAGTT TTCCCAANAA ACCACAAACN ANTGTTCATT TTTNCTCCTT     120
TTTTGTTAAC TTTTTGCCAC ACTCAANTCA GTTTAANTCC TAGCAAAAAA ACGGTAGTTA     180
GGATACCACT GTGGCTGTAA ATGATGTNAC ACTGGTTGAA TTTGTGCTGG CGTTTGTGTN     240
ACTTCCCTCG CTGTTTGTGT TTGATTCGTT AGGGGGCACC TGGCTTGAAT TGGCTCGAAN     300
GATTGCTCCT GCTGCACTGC AATGTGGCCG CGGCCCTGGT TCTGGTGTGT AAGTAAAGGT     360
AAGGCTGGTG GAATAAATGA TTCCNTCATT TCGGANCAAA GTTACTGGAA CCTGGANTGG     420
TTGNCGGACC ATCTCCAACC TTCTCGGAAT GCANAAATGT CTGGGACAAN ACNNAACATA     480
CTCTCTCCNC ACCTGGTTCA TANTTTCAGC TTCTACATCC CCCAAACCAC ACTCNTAAAT     540
TTGGANTGAA ATTCTGTCCT GTTAATTCAA ACATTGCTAC GTCCCCNCCG CCATTCAACT     600
GAAAG                                                                605
```

(2) INFORMATION FOR SEQ ID NO: 7:

(i) SEQUENCE CHARACTERISTICS:
        (A) LENGTH: 666 base pairs
        (B) TYPE: nucleic acid
        (C) STRANDEDNESS: double
        (D) TOPOLOGY: linear (xi) SEQUENCE DESCRIPTION: SEQ ID NO: 7:

```
GAAGAGTTTG TGGAAGATGG CGCCTGTTGT GACAGGGAAA TTTGGTGAGC GGCCTCCACC      60
TAAACGACTT ACTAGGGAAG CTATGCGAAA TTATTTAAAA GAGCGAGGGG ATCAAACAGT     120
ACTTATTCTT CATGCAAAAG TTGCACAGAA GTCATATGGA AATGAAAAAA GGTTTTTTTG     180
CCCACCTCCT TGTGTATATC TTATGGGCAG TGGATGGAAG AAAAAAAAAG AACAAATGGA     240
ACGCGATGGT TGTTCTGAAC AAGAGTCTCA ACCGTGTGCA TTTATTGGGA TAGGAAATAG     300
TGACCAAGAA ATGCAGCAGC TAAACTTGGA AGGAAAGAAC TATTGCACAG CCAAAACATT     360
```

-continued

```
GTATATATCT GACTCAGACA AGCGAAAGCA CTTCATGTTG TCTGTAAAGA TGTTCTATGG      420

CAACAGTGAT GACATTGGTG TGTTCCTCAN CAAGCGGATA AAAGTCATCT CCAAACCTTC      480

CAAAAAGAAC AGTCATTGAA AAATGCTGAC TTATGCATTG CCTCAGGAAC AAAGGTGGCT      540

CTGTTTAATC GACTACGATC CCAGACAGTT NGTACCAGAT ACTTGCATGT ANAAGGAGGT      600

AATTTTCCAT GCCAGTTCCC ACCAGTGGGG AGCCTTTTTT ATTCNCTCTT GGGATGATGA      660

TGAATC                                                                 666
```

(2) INFORMATION FOR SEQ ID NO: 8:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (xi) SEQUENCE DESCRIPTION: SEQ ID NO: 8:

```
GCCACACTCA AGTCAGTTTA AGTCCTAGCA AAAAGACGGT AGTTAGGATA CCACTGTGGC       60

TGTANATGAT GTGACACTGG TTGAATTTGT GCTGGCGTTT GTGTAACTTC CCTCGCTGTT      120

TGTGTTTGAT TCGTTAGGGG GCACCTGGCT TGAATTGGCT CGAAGGATTG CTCCTGCTGC      180

ACTGCAATGT GGCCGCGGCC CTGGTTCTGG TGTGTAGGTA AAGGTAAGGC TGGTGGAATA      240

AATGATTCCA TCATTTCGGA CCAAAGTTAC TGGAACCTGG ACTGGTTGCC GGACCCATCT      300

CCAACCTTCT CGGAATGCAG AAATGTCTGG GACGACACAG ANCATACTCT CTCCACACCT      360

GTACATAGTT TCAGCTTCTA CATCCCCAAA CCACACTCGT AAATTTGGAG TGAAATTCTG      420

TCCTGTAAGT TCAAGCATTG CTACGTCCCC ACCGCCATTC AACTGAAGGC TCTCTACCAC      480

AGGCACAGGA ATGACTGGGG CAAGGACAGG GCCCATTCCC TNCATAAAAT GTNTAATTTG      540

GGGNCAANTG TGGCCCCCAA CCCCCCCCCA AAGGGCATNA TTTAACNCCN CTTTAATTGG      600
```

(2) INFORMATION FOR SEQ ID NO: 9:

(i) SEQUENCE CHARACTERISTICS:
        (A) LENGTH: 835 base pairs
        (B) TYPE: nucleic acid
        (C) STRANDEDNESS: double
        (D) TOPOLOGY: linear (xi) SEQUENCE DESCRIPTION: SEQ ID NO: 9:

```
ACTGTGGCTT CTGCATTTCA AATCAGCACT TGCAGGAGA CAACGGGGTT TTTGAATAGT        60

ATCACCTGGT ATGAAAAGTT TTCCCAANAA ACCACAAACN ATTGTTCATT TTTTCTCCTT      120

TTTTGTTAAC TTTTTGCCAC ACTCAANTCA GTTTAAGTCC TAGCAAAAAN ACGGTAGTTA      180

GGATACCACT GTGGCTGTAA ATNATGTGAC ACTGGTTGAA TTTGTGCTGG CGTTTGTGTA      240

ACTTCCCTCG CTGTTTGTGT TTGATTCGTT AGGGGGCACC TGGCTTGAAT TGGCTCGAAG      300

GATTGCTCCT GCTGCACTGC AATGTGGCCG CGGCCCTGGT TCTGGTGTGT AGGTAAAGGT      360

AAGGCTGGTG GAATAAATGA TTCCATCATT TCGGACCAAA GTTACTGGAA CCTGGACTGG      420

TTGCCGGACC CATCTCCAAC CTTCTCGGAA TGCAGAAATG TCTGGGACGA CACANANCAT      480

ACTCTCTCCA CACCTGTACA TAGTTTCAGC TTCTACATCC CCAAACCACA CTCGTAAATT      540

TGGAGTGAAA TTCTGTCCTG TAAGTTCAAG CATTGCTACG TCCCCACCGC CATTCAACTG      600

AAGGCCTCTA CACAGGCACA GGAATGACTG GGGCAAGGAN AGGGCCCATT CCCTCATAAA      660

ATGTATACTC TGCCTTATCT GTGCTAATGA TTGTCCAGGA AACGCCANCA TTTTACCACC      720

TCNTTATTGG TTCTTTTGGG ANTGGAATGG CCTGAAATTG AAATATTCTT CCTTGAAAAA      780
```

```
AGGCCAAATA CNTCTTCTGT TTCCTTNAAG GGTAAAATGC CCATTTTTGG AATTG           835
```

(2) INFORMATION FOR SEQ ID NO: 10:

(i) SEQUENCE CHARACTERISTICS:
        (A) LENGTH: 443 base pairs
        (B) TYPE: nucleic acid
        (C) STRANDEDNESS: double
        (D) TOPOLOGY: linear (xi) SEQUENCE DESCRIPTION: SEQ ID NO: 10:

```
AGCAGTTCGA ATGCCAGGAA ACTGCTCGAG TGCCAGGTGC AGGTGGGGGC CCCCGAGGAG        60
GAGGAGGAGG AGGAGGAGGA CGCGGGCCTG GTGGCCGAGG CCGANGCCGT GGCTGCCGGC       120
TGGATGCTCG ATTTCCTCTG CCTCTCTCTT TGCCGAGCTT TCCGCNACGG CCGCTCCGAG       180
GACTTCCNCN GGACCCGCAA CAGCGCANAG GCTATTATTC ATGGACTATC CAGTCTAACA       240
GCTTGCCAGT GAGAACGATA TACATATGTC AGTTTTTGAC AAGAATTGCA GCAGGAAAAA       300
CCCTTGATGC NCAGTTTGAA AATGATGAAC GAATTACACC CTTGGAATCN GCCCTGATGA       360
TTTGGGGTTC AATTGAAAAG GAACATGACN AACTTCNTGA AGAAATACAG AATTTAATTA       420
AAATTCANGC TATNGCTGTT TGT                                              443
```

(2) INFORMATION FOR SEQ ID NO: 11:

(i) SEQUENCE CHARACTERISTICS:
        (A) LENGTH: 491 base pairs
        (B) TYPE: nucleic acid
        (C) STRANDEDNESS: double
        (D) TOPOLOGY: linear (xi) SEQUENCE DESCRIPTION: SEQ ID NO: 11:

```
GTACTTTGAG GAGTTCCTAC TCTTCTTTCT TTCTTATTAA GGTCTTGTTG CTGGGTTCCA        60
TGTTGCAACT TAGATAANAA AAGATTCTTG TGAGACCTCA ATAAGGATAC TGTACCCTCT       120
GAGGATTCAG TTACCGCAGA CTGTTTGTCA CTAACACTTT TCTTGTATC  CAAATTAGCT       180
TCAGTTTCCA TTTCAACATC ATTACCACTA GGTTTATCTT GAGAAGTTAT TGTTCTTGTC       240
CTTTTGCTTT CTACTACTTT TGCCGCTGCC TTCATTAGAA AGGTTGATGA TTTTTCACTT       300
AGCACATAAT TCACATAACT CTTAATTTTC TCCATCATGT GGTTGTAGCT GAAGTGTTGA       360
AAAAAGGAAT GAAATGTATC TTTCTGAGAN ATTATCATAA GCAATTTGCT TTTGAAAGGC       420
ATATGAGAAT TTGGATCACC AAATATTCTT CAAAGACTT  CTTCTGCTTC TTTAAAGTTG       480
CCATTTTCCA T                                                           491
```

(2) INFORMATION FOR SEQ ID NO: 12:

(i) SEQUENCE CHARACTERISTICS:
        (A) LENGTH: 802 base pairs
        (B) TYPE: nucleic acid
        (C) STRANDEDNESS: double
        (D) TOPOLOGY: linear (xi) SEQUENCE DESCRIPTION: SEQ ID NO: 12:

```
GTACTTTGAG GAGTTCCTAC TCTTCTTTCT TTCTTATTAA GGTCTTGTTG CTGGGTTCCA        60
TGTTGCAACT TAAATAAGAA AAGATTCTTG TGAGACCTCA ATAAGGATAC TGTACCCTCT       120
GAGGATTCAG TTACCGCAGA CTGTTTGTCA CTAACACTTT TCTTGTATC  CAAATTAGCT       180
TCAGTTTCCA TTTCAACATC ATTACCACTA GGTTTATCTT GAGAAGTTAT TGTTCTTGTC       240
CTTTTGCTTT CTACTACTTT TGCCGCTGCC TTCATTAGAA AGGTTGATGA TTTTTCACTT       300
```

```
AGCACATAAT TCACATAACT CTTAATTTTC TCCATCATGT GGTTGTAGCT GAAGTGTTGA      360

AAAAAGGAAT GAAATGTATC TTTCTGAGAG ATTATCATAA GCAATTTGCT TTTGAAAGGC      420

ATATGAGAAT TTGGATCACC AAATATTCTT TCAAAGACTT CTTCTGCTTC TTTAAAGTTG      480

CCATTTTCCA TACAAACAGC TATAGCCTGA ATTTTAATTA AATTCTGTAT TTCTTCATGA      540

AGTTTGTCAT GTTCCTTTTC AATTGAACCC CAAATCATCA GGGCTGATTC CAANGGTGTA      600

ATTCGTTCAT CATTTTCAAA CTGTGCATCA AGGGTTTTTC CTGCTGCAAT TCTTGTCAAA      660

AACTGACATA TGTNTATCGT TCTCAACTGG CNAGCCTGTT AAACTGGAAA ATCCATGAAT      720

AATAACCTCT GGCGCTGTTG CGGGTCCTGC GGAAATTCCN CGGAACCGGC CGTCNCGGAA      780

AACTCNGCAA AAGAAAAAAA GC                                              802

(2) INFORMATION FOR SEQ ID NO: 13:

(i) SEQUENCE CHARACTERISTICS:
         (A) LENGTH: 523 base pairs
         (B) TYPE: nucleic acid
         (C) STRANDEDNESS: double
         (D) TOPOLOGY: linear (xi) SEQUENCE DESCRIPTION: SEQ ID NO: 13:

GAAAAGCAAC TTTTATTGAA NAATTTGGAG GGAAGGTTCC ATATTATATT ATAATAGTAA       60

AAATACTAAA GTTGAATGTT GTAAAAAAAC NCCGTGGTGC AGCGGCAGCG GCAGCGTCTG      120

GCCAGGAGGC GTGGAGGGGC CCAGGGATGG CCACCCCCAC AGGGAGTCAG GGAGGGCCTG      180

GGGCGACAGC GGAAAGGTTA AGCGTCNAAA AGGTCAAGTG CTACCGTGGA NAAATCATCT      240

GAGGGGGAGG CTCCCGGTGG GACAGTCACC AANAACTGTN ACACACAAGG GGAAGGGGGA      300

GGGCTTTCCT GTCACAAANA TTAAAAACCC CCNAAATGCA TTTGAACAAC ATNATACACN      360

ATAACAAATT TAAACCTTGC TCCTCTGTCC CACTGGGTNA ACCCTGGCCC ATCCCCCATC      420

CCTGGTCCCA TCCCAGGGGC CCAGCCTCCG ATNACTCCTC ANAAACACNG CCTTNNTGCT      480

GGGGGGCTGC TGTNTNCCTG CCACCCCCNN GAAAAGGTGC TGG                       523

(2) INFORMATION FOR SEQ ID NO: 14:

(i) SEQUENCE CHARACTERISTICS:
         (A) LENGTH: 530 base pairs
         (B) TYPE: nucleic acid
         (C) STRANDEDNESS: double
         (D) TOPOLOGY: linear (xi) SEQUENCE DESCRIPTION: SEQ ID NO: 14:

AAAACCAACT TTTATTGAAA AATTTGGAGG GAAGGTNCCA TNTTATNTTA TAATANTAAA       60

AATACTAAAT TTAAATTTTN TAAAAAAACC CCNTGNTGCA CCGGCANCGG CANCTTCTGG      120

CCAAAANGCT TNAAGGGGCC CAGGGATNGC CNCCCCCNCA GGGATTCNGG GAGGGCCTGG      180

GGCAANANCG NAAAGGTTAA CCNTCNAAAA GGTCAATTNC TACCGTGNAA AAATNATCTN      240

AGGGGGANGC TCCCGGTGGG ACACTCCCCN AAAACTNTNA CCCAAAAGGG GAAGGGGGAG      300

GGCTTTCCTN TNNCAAAAAT TNAAANCCCC CNAAATGCCT TTNAACNACT TTNTNCCCAN      360

TNNCAATTTT NAACCTTGCN CCTCTNTCCC ACTGGGTNAA CCCTGGCCCA TCCCCCATCC      420

CTGGTCCCNT CCCNGGGGCC CACCCCCCNA TAACTTCCTC AAAAACCNGC CTTNTTNCTG      480

GGGGGCTGCT NTTTTCTTCC CCCCCAANA AAAGGTNCTG GCCCCCCTCC                  530

(2) INFORMATION FOR SEQ ID NO: 15:
```

(i) SEQUENCE CHARACTERISTICS:
    (A) LENGTH: 311 base pairs
    (B) TYPE: nucleic acid
    (C) STRANDEDNESS: double
    (D) TOPOLOGY: linear (xi) SEQUENCE DESCRIPTION: SEQ ID NO: 15:

| | | | | | |
|---|---|---|---|---|---|
| GCCNANCAGG | NANCCGCCGC | TGAAGCCACC | GCCGGGTGCC | CAGCGCCGCC | GCCGCCCCCG | 60 |
| AGCTCCCCCG | CGCCCCTGCC | CNCGGGCGGN | CGGTGGGCAC | CGGGCGCCAT | GGCCGCGCCG | 120 |
| GGANCCGCTG | CGGNTNCGCN | TGTGCCNCTT | GGTGCNCGGA | ANANCANGGC | TACNGNTTCT | 180 |
| ACCTNTACGT | GTGANANNGG | CCGCCGCGGG | CACTTCNTCC | GGCGCGTGNA | NCCTCTGTTC | 240 |
| CCCCGCCGAG | GCNGCCGCGC | TGTGCTCTGG | GGATCTNCTG | NTCNAGGTCA | ACNTGCNTCA | 300 |
| ACGTGNAGGG | C | | | | | 311 |

(2) INFORMATION FOR SEQ ID NO: 16:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (xi) SEQUENCE DESCRIPTION: SEQ ID NO: 16:

| | | | | | |
|---|---|---|---|---|---|
| GCANAGAAAG | GTTTGTTTTA | TTGCAATTAT | TTAAATCNCG | TCCCANGGGG | GAGGGGAAGG | 60 |
| GGGANGGGAA | GGGGGGGGTN | TCTGGTNTTN | ATTNGATNCC | TGTCTGCCAN | CTTNNACATC | 120 |
| TATNANGAAN | ANAACCATCA | NCNCNCNTCC | CTTTCANTCA | TCTGGCNCCT | GCANACCATC | 180 |
| TTTCGCCCTC | TNCCCCCGC | TGCTCTCCNA | CTCCCNTGAC | CNCTCTCATC | TCTCTCCNCT | 240 |
| CTGNCTCCTC | NCTCTNTCTC | TCATTTCTCT | GTTNCACNCT | CTCTCCCCC | | 289 |

(2) INFORMATION FOR SEQ ID NO: 17:

(i) SEQUENCE CHARACTERISTICS:
        (A) LENGTH: 356 base pairs
        (B) TYPE: nucleic acid
        (C) STRANDEDNESS: double
        (D) TOPOLOGY: linear (xi) SEQUENCE DESCRIPTION: SEQ ID NO: 17:

| | | | | | |
|---|---|---|---|---|---|
| CTGAAGCCAC | CGCCGGGTGC | CCAGCGCCGC | CGCCGCCCCC | GAGCTCCCCC | GCGCCCCTGC | 60 |
| CCGCGGGCGG | CCGGTGGGCA | TCGGGCGCCA | TGGCCGCNCC | GGANCCGCTG | CGGCCGCGCC | 120 |
| TGTGCCGCTT | GGTGCGCGGA | NAGCANGGCT | ACGGCTTCCA | CCTGCACGGT | GAGAANGGCC | 180 |
| GCCGCGGGCA | NTTCATCCGG | CGCGTGGAAC | CCGGTTCCCC | CGCCGAGGCC | NCCGCNCTGC | 240 |
| GCGCTGGGGA | CCGCNTGNTC | NAGGTCNACN | GCGTCAACNT | GGAGGGCGAT | ACCACCNCCT | 300 |
| NGTGNTGCNT | ACGATCNANG | CTGTNGANGG | GCANACTCGG | CTGCTGGTGG | TGGACC | 356 |

(2) INFORMATION FOR SEQ ID NO: 18:

(i) SEQUENCE CHARACTERISTICS:
        (A) LENGTH: 290 base pairs
        (B) TYPE: nucleic acid
        (C) STRANDEDNESS: double
        (D) TOPOLOGY: linear (xi) SEQUENCE DESCRIPTION: SEQ ID NO: 18:

| | | | | | |
|---|---|---|---|---|---|
| GCAAAGAANG | GTTTGTNTTA | TTGCAATTAT | TTANAGCGCG | TCCCAAGGGG | GAGGGGANGG | 60 |
| GGGANGGGAA | GGGGGGGGTN | TCTTGCTANA | AACTGGAAAC | NTGTTTCTTA | CCCCNATNTC | 120 |

```
NNANTCGACT NCCACCAACT GTNNNTCTTC CTTCCTTTCC CNANGTCCCT ANNTACCNCC        180

TNTTGCCCTT CTNCCCCTTN TTTCCCCTCN CGCTTTCCCT NACTCTTTAT CTNTCTTNTC        240

CTCTCTCTCT CTCACCTCTT TCTCCCCCTC CCTTCACNCT CACNTTGTCT                   290
```

(2) INFORMATION FOR SEQ ID NO: 19:

(i) SEQUENCE CHARACTERISTICS:
        (A) LENGTH: 714 base pairs
        (B) TYPE: nucleic acid
        (C) STRANDEDNESS: double
        (D) TOPOLOGY: linear (xi) SEQUENCE DESCRIPTION: SEQ ID NO: 19:

```
CGCCAGAAAA AGTTATTTTA ATTTTCTATT AAACATTCTT CTCAAAGCAT TATTTTATCC         60

TATATCTCAC TGAATTTTAA GAAATAACAT TAGTATTAGA AAAACTAGGA AAAAGATAA        120

ATGCAGATAA TTAAACTTAC ATGAAAAAGG AAAATTATAA CAAAGGACTG AGAACGTTAT       180

AAATTGAAAT GAGATTATAA TTTGAAAACT GCATCTGAAA GCAAACTTTA TTGTTCAATT       240

ATNCTTAATG ATGGTGTTTT ATGACTAATA CACTGATTTT TCAAGAAGGA AACCCATGTT       300

AAAAATATTT TTATTTTAAA AATAAGCCTG TGTTCAAGCT CTGATCATAT TTCTTTTATT       360

TTGATTTGGG AANAAAATAC TGTTTCTGAT AGCATGAAAT GCAAAATTTT TAGATTTTTA       420

ATCTCACTAA TTTTAANAAC TATTGAGAAA TTGATTAATG ACATGAAGTG CACAACACTA       480

ATTACTGGCC AGCTGTTGGC ATTGTGTTTC TTACTTAGTT CTCCCAAGGG AAAACTCTTA       540

AATTGAATCT TCAGCAGAAT AATCCTTAAA TATACTTTGT AAGCAAAACA AAAGCTTTTT       600

TGTTTACATA GTTCTTTGGG ATTTTACTGT TCCTAATTTT ATTCTGAAAC TCAATTTTAC       660

CCCAGACCAT AATTACCATA TTAACTTTGT TNTGCACAGT TGTTTGCCAA TTCA            714
```

(2) INFORMATION FOR SEQ ID NO: 20:

(i) SEQUENCE CHARACTERISTICS:
        (A) LENGTH: 687 base pairs
        (B) TYPE: nucleic acid
        (C) STRANDEDNESS: double
        (D) TOPOLOGY: linear (xi) SEQUENCE DESCRIPTION: SEQ ID NO: 20:

```
ATTTTAATTT TCTATTAAAC ATTCTTCTCA AAGCATTATT TTATCCTATA TCTCACTGAA        60

TTTTAANAAA TAACATTAGT ATTAGAAAAA CTAGGAAAAA AGATNAATGC AGATAATTAA       120

ACTTACATGA AAAGGAAAA TTATAACAAA GGACTGAGAA CGTTATAAAT TGAAATGAGA       180

TTATAATTTG AAAACTGCAT CTGAAAGCAA ACTTTATTGT TCAATTATTC TTAATGATGG       240

TGTTTTATGA CTAATACACT GATTTTTCAA TAAGGAAACC CATGTTAAAA ATATTTTTAT       300

TTTAAAAATA AGCCTGTGTT CAAGCTCTGA TCATATTTCT TTTATTTTGA TTTGGGAAGA       360

AAATACTGTT TCTGATAGCA TGAAATGCAA AATTTTTAGA TTTTTAATCT CNCTAATTTT       420

AAGAACTATT GAGAAATTGA TTAATGACAT GAAGTGCACA ACACTAATTA CTGGCCAGCT       480

GTTGGCATTG TGTTTCTTAC TTAGTTCTCC CAAGGAAAAC TCTTAAACTG AATCTTCAGC       540

NGAATAACCT TAAATATACT TGTTAGCCA AACAAAACTT TTTTGTTTAC ATAGTTCTTT       600

GGATTTTACT GTTCCTAATT TTATTCTGAA ACTCCATTTT TCCCCAGACC ATAATTACCC       660

TATTTAACTT TGTTATGCAC AGTTGTT                                          687
```

(2) INFORMATION FOR SEQ ID NO: 21:

(i) SEQUENCE CHARACTERISTICS:
    (A) LENGTH: 994 base pairs
    (B) TYPE: nucleic acid
    (C) STRANDEDNESS: double
    (D) TOPOLOGY: linear (xi) SEQUENCE DESCRIPTION: SEQ ID NO: 21:

| | | | | | |
|---|---|---|---|---|---|
| CTCACCCAGT | TGCTCCTCAG | ATGTTTGGGT | ATGCTGGAAA | AGAACATATG | GAAAAATATG | 60
| GAACAAAAAT | TGAACACTTT | GCAAAAATTG | GATGGAAAAA | TCATAAACAT | TCAGTTAATA | 120
| ACCCGTATTC | CCAGTTCCAA | GATGAATACA | GTTTAGATGA | AGTGATGGCA | TCTAAAGAAG | 180
| TTTTTGATTT | TTTGACTATC | TTACAATGTT | GTCCCACTTC | AGATGGTGCT | GCAGCAGCAA | 240
| TTTTGGCCAG | TGAAGCATTT | GTACAGAAGT | ATGGCCTGCA | ATCCAAAGCT | GTGGAAATTT | 300
| TGGCACAAGA | AATGATGACT | GATTTGCCAA | GCTCGTTTGA | AGAAAAAGC  | ATTATTAAAA | 360
| TGGTTGGCTT | TGATATGAGT | AAAGAAGCTG | CAAGAAAATG | CTATGAGAAA | TCTGGCCTGA | 420
| CACCAAATGA | TATTGACGTA | ATAGAACTTC | ACGATTGCTT | TTCTACCAAC | GAACTCCTTA | 480
| CTTATGAAGC | ACTGGGACTC | TGTCCAGAAG | GACAAGGTGC | AACGCTGGTT | GATAGAGGAG | 540
| ATAATACATA | TGGAGGAAAG | TGGGTCATAA | ATCCTAGTGG | TGGACTGATT | TCAAAGGGAC | 600
| ACCCACTAGG | CGCTACAGGT | CTTGCTCAGT | GTGCAGAACT | CTGCTGGCAG | CTGAGAGGGG | 660
| AAGCCGGAAA | AGAGGCAAAG | TTCCTGGTGC | AAAGGTGGCT | CTGCNGCATA | ATTTANGCAT | 720
| TGGAGGAACT | GTGGTTGTAA | CACTCTACAA | GATGGGGTTT | TCCCGGAAGC | CGCCAGTTCC | 780
| TTTTAGAACT | CATCAAAATT | GAAGCCNGTT | CCAACCAAGC | TCTGCAAGTN | ATNGGTTTAA | 840
| NGNAAAATCT | NGTTTTAAAG | GNGGATTGAG | AAGGAAACNT | NAAAGAGGGA | ANGGGGAACA | 900
| ATTTGTGAAA | GAAAAATNCG | GNGGGAATTT | TTGCCCTTCA | AGGGGAAANA | ATGGCCCTGG | 960
| GGGGTAAAAG | ANGGCCACCC | TGGGGTGGTG | GGAT       |            |            | 994

(2) INFORMATION FOR SEQ ID NO: 22:

(i) SEQUENCE CHARACTERISTICS:
        (A) LENGTH: 843 base pairs
        (B) TYPE: nucleic acid
        (C) STRANDEDNESS: double
        (D) TOPOLOGY: linear (xi) SEQUENCE DESCRIPTION: SEQ ID NO: 22:

| | | | | | |
|---|---|---|---|---|---|
| GGCCAAAAAA | ANTTATTTNA | ATTTCCTATT | AANCNTCCTC | CNCAAANCAT | TATTTNACCC | 60
| TATNNCNCNC | NGANTTTNAN | AAANTACCTT | TNNTNTTAAA | AAACCTNGGA | AAAAAAATAA | 120
| TNGCAAATAN | TTAACCTTNC | TTGAAAANGG | AAATTTNTAC | CAANGGACNG | AAANCNTTNT | 180
| AATTNGAANT | NAAATTATAN | TTNGAAANCG | GCNNCNGAAA | CCAANCTTNA | TGGTCCAATT | 240
| ATCCTNAANG | AGGGNNTTTN | ANNACTAATN | CCCNGATTTT | CCAATANGGA | ANCCCNNNTT | 300
| AAAANTNTTT | TNATTTTAAA | AATAACCCNG | TNTCCAACCC | CNGATCANAT | TCCTTTNATT | 360
| TGGATTGGGG | AAAAAAATNC | NGTTCCNNAT | ACCNNGAANN | GCAAANTTTT | TAAATTTTA  | 420
| ACCCCCCTAN | TTTTAAAANC | TATNGAAAAN | TNGATTANNG | ACTTGAATTG | CCAACCCTAN | 480
| TTNCNGGCCA | CCNGTGGGCN | TNGTNTTCCT | TACTTANTCC | CCCCAAGGAA | ANNCCTTAAN | 540
| CNGAANCTCC | NCCAAAATAA | CCCTTAANTA | TCCTTGGTAA | CCAAANCAAA | ACCTTTTTNG | 600
| TTTACNTANT | CCTTGGGATT | TAACGGGTCC | CCAATTTNAT | CCNGAACCCA | NTTTTCCCCC | 660
| NAACCATANT | TACCATTTTA | CCTTGGTAAG | GCNCAGTNGT | TTGCANTNCC | GCAAANCAGT | 720
| ANTNTTCCCC | NGGCNCTTTC | CCCCGANCCT | TGGGAAAAAC | GGGATNGGTC | CCCCCCTTAA | 780

```
AAAACAACCT TCCCCCNCCT TTGGCCCAGG NNTTNTTCCC GTCTAAATCC GAACAATAAA      840

AAG                                                                    843

(2) INFORMATION FOR SEQ ID NO: 23:

(i) SEQUENCE CHARACTERISTICS:
        (A) LENGTH: 707 base pairs
        (B) TYPE: nucleic acid
        (C) STRANDEDNESS: double
        (D) TOPOLOGY: linear (xi) SEQUENCE DESCRIPTION: SEQ ID NO: 23:

CTAGTCTCGA GTTTTTTTTT TTTTTTTTAA CCTTTCCTTA TGAGCATGCC TGTGTTGGGT       60

TGACAGTGAG GGTAATAATG ACTTGTTGGT TGATTGTANA TATTGGGCTG TTAATTGTCA      120

GTTCAGTGTT TTAATCTGAC GCAGGCTTAT GCGGAGGANA ATGTTTTCAT GTTACTTATA      180

CTAACATTAG TTCTTCTATA GGGTGATAGA TTGGTCCAAT TGGGTGTGAG GAGTTCAGTT      240

ATATGTTTGG GATTTTTTAG GTANTGGGTG TTGAGCTTGA ACGCTTTCTT AATTGGTGGC      300

TGCTTTTAGG CCTACTATGG GTGTTAAATT TTTTACTCTC TCTACAAGGT TTTTTCCTAG      360

TGTCCAAANA GCTGTTCCTC TTTGGACTAA CAGTTAAATT TACAAGGGGA TTTAGAGGGT      420

TCTGTGGGCA AATTTAAAGT TGAACTAAGA TTCTATCTTG ACAACCAGC  TATCACCAGG      480

CTCGGTAGGT TTGTCGCCTC TACCTATAAA TCTTCCCACT ATTTTGCTAC ATAGACGGGG      540

TGTGCTCTTT TANCTGTTCT TANGTANCTC GTCTGGTTTC GGGGGTCTTA GCTTTGGCTC      600

TCCTTGCAAA GTTATTTCTA AGTTNAATTC ATTATGCNCA ANGTATAGGG GTTAGTCCTT      660

GCTCATATTA TGCTTGGTTA TAATTTTCCA NCTTTCCCCT TGCGGTA                    707

(2) INFORMATION FOR SEQ ID NO: 24:

(i) SEQUENCE CHARACTERISTICS:
        (A) LENGTH: 663 base pairs
        (B) TYPE: nucleic acid
        (C) STRANDEDNESS: double
        (D) TOPOLOGY: linear (xi) SEQUENCE DESCRIPTION: SEQ ID NO: 24:

CCATTTTATA ATGCGCTTTA TTTGATTAAA GAATTTGCCT TCTTTGTATA CACTGGAATG       60

TTATATTCCC TATGTATTTT ACAGGGTTAC AAAATGTCTC TCATTTTAAA TATTACCCCA      120

AAAGTAATCT CANAAAAAAA AGGTTTTTTG AAATTAAACT TGACTTTTAA AAAATCATAC      180

GGACAAACAA CTTTCAAACA AAACTGGATT AGTAGGATTT CTTGCCTGCT TAACTAACAT      240

GACANACTTC TTGTCCCAGG CCCTTCTCAN AAAAACCTCA TGTGGAAACC AAGCTANAGA      300

TAANAATTCT TCCCTGATGC AGTTAGGGGA AAGGGAAAGG CTAGAAACTT CTTTGGCAAG      360

CAATTCCACA CACAGCCATT TATGTGTGAG TGCTCTGCTT CAAGCACAGT ACGCTCTTTG      420

CAGGGACGGC CAGATGTTCA GAGTGGGAGT GGTACTTTTC AACCAGCTAA AAGTGCAGAA      480

GTCATCTANT CGTCTGCCTC TTCCCACTGC CAGTGCCTGC AGCCTTGCAG CAACTTTTAA      540

CCACCCCCTA TGGGACTGGA ATNTTGAGTT AAAAAGCCAA NGCTGAACTG GCTGACGCTG      600

TANTCTCCAN TGAAAGGAA  ATGGGATGAA ATGGAAACCG AAAAACCCCC NGTNACNTGA      660

TGA                                                                    663

(2) INFORMATION FOR SEQ ID NO: 25:

(i) SEQUENCE CHARACTERISTICS:
```

(A) LENGTH: 621 base pairs
        (B) TYPE: nucleic acid
        (C) STRANDEDNESS: double
        (D) TOPOLOGY: linear (xi) SEQUENCE DESCRIPTION: SEQ ID NO: 25:

CATTTTATAA TGCGCTTTAT TTGATTAAAG AATTTGCCTT CTTTGTATAC ACTGGAATGT     60

TATATTCCCT ATGTATTTTA CAGGGTTACA AAATGTCTCT CATTTTAAAT ATTACCCCAA    120

AAGTAATCTC ANAAAAAAAA GGTTTTTTGA AATTAAACTT GACTTTTAAA AAATCATACG    180

GACAAACAAC TTTCAAACAA AACTGGATTA GTAGGATTTC TTGCCTGCTT AACTAACATG    240

ACAAACTTCT TGTCCCAGGC CCTTCTCANA AAAACCTCAT GTGGAAACCA AGCTANANAT    300

ANAATTCTT CCCTGATGCA GTTAGGGGAA AGGGAAAGGC TAGAAACTTC TTTGGCAAGC     360

AATTCCACNC ACAGCCATTT ATGTGTGAGT GCTCTGCTTC AAGCACANTA CGCTCTTTGC    420

AGGGACGGCC ANATGTTCNN ANTGGGAGTG GTACTTTTCA ACCAGCTAAA ANTGCANAAG    480

TCATCTANTC GTCTGCCTCT TCCCACTGCC AGTTGCCTGC AGCCTTGCAG CATCTTTTAA    540

CCACCCCTAT NGGACTGGAA TATTGAATTA TAAACCCNGG NTGAACTGGC TGANGCTGTT    600

TCTCCCTTGA AAAGGAAATG G                                              621

(2) INFORMATION FOR SEQ ID NO: 26:

(i) SEQUENCE CHARACTERISTICS:
        (A) LENGTH: 637 base pairs
        (B) TYPE: nucleic acid
        (C) STRANDEDNESS: double
        (D) TOPOLOGY: linear (xi) SEQUENCE DESCRIPTION: SEQ ID NO: 26:

CATTTNATAA TGCGCTTTAT NTGATTAAAN AATNNGCCTT CTTTGTATAC GCNGGATTGT     60

TATCTCCCCT NTNTATTTNN GGGGGTTACA ANTTNTCNCT CATTTNAANT ATNNCCCCAA    120

TANTNTNCTN AAAAAAAAGA GGTTTGANGA AATTAAACTT GACTTTTAAA ANATCATGNG    180

GACAAACNAC TTTCAAACAA AGCTGGATTA GNAGGATTTC TNGNCTGCTT AACTAACATN    240

AAANACTTCT TGTCCCAGGC CCTNCTNAAA AAAACCTCTT GTGGAAACCN AGCNAAAAAT    300

AANANTTCTC CCCTGATGCA NTGGGGGAG ANGGAGAGGC TAAAAACTTC TNTGGCAANC     360

ANTTCCACNC ACNGCCATTT TTNTNTNAGT GCNCTGCTNC NANCNNAGTA CGCTCTTTGG    420

GNGGACGGCN ANNTNTTTAT AGNGGAGTG GTNCTTTCAA CCAGCTAATA NTGAAGAAAT     480

CATCTAGTCG NCTGCCTCTN CCCACTGCCA GTGCCTGCNT CCTTGCAACN TCTTTTAACC    540

CCCCCTANGG ACNGGATTAT NNAGTTAANA CCGAGGNTGA GCTGGNTGAC GCTNTCTCCT    600

CCATTTGAAA ANGAAATGGA TAAGATGGAA CCGAAAA                             637

(2) INFORMATION FOR SEQ ID NO: 27:

(i) SEQUENCE CHARACTERISTICS:
        (A) LENGTH: 673 base pairs
        (B) TYPE: nucleic acid
        (C) STRANDEDNESS: double
        (D) TOPOLOGY: linear (xi) SEQUENCE DESCRIPTION: SEQ ID NO: 27:

AGATTATGCC ATTGAGGCTA AGAATAGAGT CATTTTTGAT CTAATTTATG AATACGAAAG     60

AAAGAGATAT GAAGATCTTC CTATAAATAG CAATCCAGTG TCTTCTCAGA ACAACCAGC    120

CTTGAAGGCT ACAAGTGGCA AGGAAGATTC TATTTCAAAT ATAGCCACAG AAATAAAGGA    180

| | |
|---|---|
| TGGACAAAAA TCTGGGACAG TGTCTTCTCA GAAACAACCG GCCTTGAAGG ATACAAGTGA | 240 |
| CAAGGATGAT TCTGTTTCGA ACACAGCCAC AGAAATAAAA GATGAACAAA AATCTGGGAC | 300 |
| AGTGCTTCCT GCTGTTGAAC AGTGTTTAAA CAGGAGTCTC TACAGACCTG ATGCTGTTGC | 360 |
| ACAGCCTGTG ACAGAGAATG AGTTTTCTTT GGAATCTGAG ATTATTTCAA AACTATACAT | 420 |
| CCCAAAGAGA AAGATTATTT CTCCACGATC TATAAAAGAT GTGCTTCCTC CTGTTGAAGA | 480 |
| GGCTGTTGAC AGGTGTCTCT ACCTACTGGA CCGTTTTGCA CAGCCTGTGA CAAAGGGATA | 540 |
| AGTTTGCTTT GGAATCTGAG AATATTTCAG AACCATACTT TACGAACAGA AGGACTATTC | 600 |
| TCAACAATCT GCAGAAAATT TAGATGCTGC ATGTGGCATT GACAAAACAG AAAATGGANA | 660 |
| CATGTTTGAA GAC | 673 |

(2) INFORMATION FOR SEQ ID NO: 28:

(i) SEQUENCE CHARACTERISTICS:
        (A) LENGTH: 714 base pairs
        (B) TYPE: nucleic acid
        (C) STRANDEDNESS: double
        (D) TOPOLOGY: linear (xi) SEQUENCE DESCRIPTION: SEQ ID NO: 28:

| | |
|---|---|
| CCTCTGGCTA TATTCAAAAC AGAATCTTTC TCATCACTTG AAGCCTTCAA GCCTGGTGGT | 60 |
| TTCTCANAAN ACACTGTCCT AGATTTTTCT CCATCCTTGT TTTCTCTGGC TATACCCAAA | 120 |
| ACAGAATCTT CCTCGTCACT TGTACCCTTC AAGGTTGGTG GTTTCTGANA ANACACTTTC | 180 |
| CTANATATTT CTCCATCCTT TTTTCCTCTG GTTATATTCG AAAAANAATC CTTCTCATCA | 240 |
| CTTGTAGCCT TCGAGGCTGG TTTTTTCCGA NAAGACACTG TCCTANATTT TTCTCCATCC | 300 |
| TTGTTTTCTC TGGCTATACT CAAAACAGAA CCTTCCTCGT CACTTGTANC CGTCAAGGCT | 360 |
| GGTGGTTTCT GANAANACAC TGTCCCANAT TTTTCTCCAT CCTTTATTTC TGTGGCTATG | 420 |
| TTCGAAACAG AATCTTTCTC ATCAGTTGTA GCCTTCAAGG NTGGTTGTTT CTGAAAANAN | 480 |
| CTGTCCCANA TTTTTCTCCA TCCTTTATTT CTGTGGCTAT NTTCGAAACA GAATCTTCCT | 540 |
| CGTCAGTTGT ACCTTCNAGG NTGGTTGTTT CTGAAAAAAN ACTGTCCCAC ACTGTATCCA | 600 |
| TCCTTTTATT TNTGTTANCT ATATCNAAGC AAAATCTGTT TTGTCCCTTG TTACCNTTTG | 660 |
| AAGGTNGGTN GTTTCTGAAA ATAANCTGT TCCANATTTT CCCACCACCC ATTT | 714 |

(2) INFORMATION FOR SEQ ID NO: 29:

(i) SEQUENCE CHARACTERISTICS:
        (A) LENGTH: 688 base pairs
        (B) TYPE: nucleic acid
        (C) STRANDEDNESS: double
        (D) TOPOLOGY: linear (xi) SEQUENCE DESCRIPTION: SEQ ID NO: 29:

| | |
|---|---|
| CCTCTGGCTA TATTCAAAAC AGAATCTTTC TCGTCACTTG TAGCCTTCAA GCCTGATGGT | 60 |
| TTCTCANAAN ACACTGTTCT ANATTTTTCT CCATCCTTTT TTTCTCTGGC TATATTCAAA | 120 |
| ACANAATCTT CCTCGTCACC TGTAGCCTTC AAGGCTGGTG GTTTCTGAAA ANACACTGTC | 180 |
| CTANATGTTT CTCCATCCTT TCTTTCTCTG GTTATATTTG AAAAANAATC TTTCTCATCA | 240 |
| CTTGTAGCCT TCAAGGCTGC TTTTTTCCGA NAANACACTT CAAGCCTGGT GGTTGCTCTG | 300 |
| AAAACACTGT TCTAAATTTT TCTCCATCCT TTTTTTCTCT GGCTATATTC AAAACANAAT | 360 |
| CTTCCTCGTC ACTTGTAGCC TTCAAGGCTG GTGGTTTCTG AAAANANACT GTCCTANATG | 420 |
| TTTCTCCATC CTTTCTTTCT CTGGTTATAT TTGAAAAANA ATCTTTCTCA TCACTTGTAN | 480 |

```
CCTTCAAGGN TGCTTTTTTC CGANAANAAA CTTCAAGCCT GGTGGTTGCT CNGAAAAAAC        540

TGTCCTAAAA TTTTTCTCCA TCCTTTTCTT CTCTNGGCTA TACTCNAAAC AAAATCNTCC        600

TCGTCCCTTG TTNCCCTTCA ANGGTGGGTG GTTTCTCGAA AAAAANACTG TCCTANAATT        660

TTCCTCCNTC CCTTTTTTTC TCTGGGTT                                          688

(2) INFORMATION FOR SEQ ID NO: 30:

(i) SEQUENCE CHARACTERISTICS:
        (A) LENGTH: 721 base pairs
        (B) TYPE: nucleic acid
        (C) STRANDEDNESS: double
        (D) TOPOLOGY: linear (xi) SEQUENCE DESCRIPTION: SEQ ID NO: 30:

TTCGGGCTTC CACCTCATTT TTTTCGCTTT GCCCATTCTG TTTCAGCCAG TCGCCAAGAA         60

TCATGAAAGT CGCCAGTGGC AGCACCGCCA CCGCCGCCGC GGGCCCCAGC TGCGCGCTGA        120

AGGCCGGCAA GACAGCGAGC GGTGCGGGCG AGGTGGTGCG CTGTCTGTCT GAGCAGAGCG        180

TGGCCATCTC GCGCTGCGCC GGGGGCGCCG GGGCGCGCCT GCCTGCCCTG CTGGACGAGC       240

AGCAGGTAAA CGTGCTGCTC TACNACATGA ACGGCTGTTA CTCACGCCTC AAGGAGCTGG       300

TGCCCACCCT GCCCCAGAAC CGCAAGGTGA GCAAGGTGGA GATTCTCCAG CACGTCATCG       360

ACTACATCAG GGACCTTCAG TTGGAGCTGA ACTCGGAATC CGAAGTTGGA ACCCCCGGGG       420

GCCGAGGGCT GCCGGTCCGG GCTCCGCTCA GCACCCTCAA CGGCGAGATC AGCGCCCTGA       480

CGGCCGANGT GAGATCCAGA TCCGACCACT ANATCATCCT TATACCGACG GGAAACNGA        540

AGCCATANAA GGCGTGGGCG CTTGCACCAC TTCCGTCCCA TCCTTGCGGG TACCTGGTCT       600

ATGCNGGGGT NCCTAAGGAC CTTGGAAAAA ACGCTCCCCC GTCGTTGCTT CCTGGGGAAN       660

GGGGCGTTNC GCTGCGCTTC GGAACGGGGT TCCTTCCAAC CCGCCGGTCT CATTTCTTCT       720

C                                                                      721

(2) INFORMATION FOR SEQ ID NO: 31:

(i) SEQUENCE CHARACTERISTICS:
        (A) LENGTH: 461 base pairs
        (B) TYPE: nucleic acid
        (C) STRANDEDNESS: double
        (D) TOPOLOGY: linear (xi) SEQUENCE DESCRIPTION: SEQ ID NO: 31:

CCACCANCTA ANTTATTNNT TTAATAACAA AAAAACANCC CCACAAAACT ATNGTAAAAC         60

AATATTTCCA NTCGGTNATC NTNGTATTNT ACAATACAAA NCANTTCCCN CAAAATTCTN       120

AAAANCACCA ANCTTNACCA TTTTTTAAAN TTTCTGCTTT NCAAAAANTA AAAACNCNCA       180

ATTGNANTCC CACCCCCTAA ATTCTCTGGT NACTATTAGG TNTNCAAAAA GNACCNCCCN       240

CTCCNCNCCA TTGCCTCANC CNCANCCCCA GGCTGNATNC ATTTAAGGGC NCATTGGCCG       300

CCAATCGGNC TNNTCCNCCC NCAAATCCGG CAAGGCNCTT NGGGGNAAAC CCACAAANCA       360

CTTATTCCCC CTNGCCCCCT GAATGGCTGG GGTCCGCCGG TCCCTGGGGN AGGCNCTCCA       420

CCAACNCAAA ATGCAATCNT CCNCAGNAAC CCNTGCCGCC T                          461

(2) INFORMATION FOR SEQ ID NO: 32:

(i) SEQUENCE CHARACTERISTICS:
        (A) LENGTH: 751 base pairs
        (B) TYPE: nucleic acid
```

(C) STRANDEDNESS: double
        (D) TOPOLOGY: linear (xi) SEQUENCE DESCRIPTION: SEQ ID NO: 32:

```
CCCGAGGGAC CACAGCTGGC AGCTCCGGGG ATGCCCTCGG CAAAGCACTG GCCTCGATCT      60

ACTCCCCGGA TCACTCAAGC AATAACTTCT CGTCCAGCCC TTCTACCCCC GTGGGCTCCC     120

CCCAGGGCCT GGCAGGAACG TCACAGTGGC CTCGAGCAGG AGCCCCCGGT GCCTTATCGC     180

CCATCTACGA CGGGGGTCTC CACGGCCTGC AGAGTAAGAT AGAAGACCAC CTGGACGANG     240

CCATCCACGT GCTCCGCAGC CACNCCGTGG GCACAGCCGG CGACATGCAC ACGCTGCTGC     300

CTGGCCACGG GGCGCTGGCC TCAGGTTTCA CCGGCCCCAT GTCACTGGGC GGGCGGCACG     360

CAGGCCTGGT TGGAGGCAGC CACCCCGAGG ACGGCCTCGC AGGCAGCACC AGCCTCATGC     420

ACAACCACGC GGCCCTCCCC AGCCAGCCAG GCACCCTCCC TGACCTGTCT CGGCCTCCCG     480

ACTCCTACAG TGGGCTAGGG CGANCAGGTG CCACNCGGC CGCCANCGAG ATCAAGCGGG      540

AAGAGAAGGA NGACGANGAG AACACGTCAG CGGCTGANCA CTCGGAAGAA GANAANAAGG     600

AACTGAAGGC CCCCGGGCCC GGACCATTAC GGAACAAGTG CTGTCCCTTG NAGGAGAAAA     660

ACTGAAGGAC CGGGAAAAGG CNCATGGCAA TTACNCCCCG GGAACCGGTG CCCTTCCGGG     720

ATATTAACNA AGGCTTCCGG GAACTGGGGG C                                   751
```

(2) INFORMATION FOR SEQ ID NO: 33:

(i) SEQUENCE CHARACTERISTICS:
        (A) LENGTH: 556 base pairs
        (B) TYPE: nucleic acid
        (C) STRANDEDNESS: double
        (D) TOPOLOGY: linear (xi) SEQUENCE DESCRIPTION: SEQ ID NO: 33:

```
AATACAACGT TTAATCATCT GGTTGATCAA AAAATGCAAT GCTCAGTCTA GGAACAGCAG      60

CAAAAATAGC GANAGACACG GGACTTTTAT ACAAAAAAAT TTGTTGCTTA CAAAACATAT     120

GCAAAAAAAG CTTAAAAAAA CCAAAAACCA AAGGCAGCAT CCTTGCTAAT TTTCATCTAC     180

ATTAANAAAA AAAAAATCTT GTAACTAATG TTTTTATTTN CCTTAAAAAA AATATTTCGC     240

TTAGGCACAA TTTGCTGGTG GCTTTAAAAA AATAAGCCAG GTTTCCACAG CATCCCCCTT     300

GAGTGATATN TTTCCATTTC TCCGCTTTTT ATAGTTAAGG CATTTTTTNC TNCTCTGACA     360

AAGTGTATGT TTTGTTGCTT GCTTTCAGGT TTTGTTTACT GGAAAAAAAA AAAAATGCCC     420

TGTCANCCCA NGCAANAGGG CCAANATGCA ATTCAGGGAT CCNTGGGACA GGTCCAAAAT     480

GACCCGGGGG CTGAAATTCC GGGACGGGGG AACAAGGCNN TTTAATNGTA GGCCAGGGCC     540

CANGGAACCC TGAACC                                                    556
```

(2) INFORMATION FOR SEQ ID NO: 34:

(i) SEQUENCE CHARACTERISTICS:
        (A) LENGTH: 708 base pairs
        (B) TYPE: nucleic acid
        (C) STRANDEDNESS: double
        (D) TOPOLOGY: linear (xi) SEQUENCE DESCRIPTION: SEQ ID NO: 34:

```
CCACTTNAAT TCCTTTATNC ANCAATATTA TCCNAAAAGG AAAAATCAGG ATTTACAAAA      60

ACAATTTAAN TGCAATATAA AACCCTACTA AATACAAATA CAATTNCACA AACNCNTATG     120

CAACAAAAAC TTGTTTAAAT NGTTCCTTNA ATTTNNACTA CTTAAAANCA TAGGTNTAAA     180
```

```
GGAAAAACNT NCAAACTGGT CCACTTGGGC TTNTTACCAG GCAAAGNAAC CCTGCTTNCC      240

AAAAACTNAT ATATTCCAAA TTCNCGGCAT NTGGNAATNT TNCCATGGAC NCTGNATCTT      300

AACAAATGCT ATANTNTTTA CAAAACTACN CCCNCAAAAA AACCCCAAGG AACCTGCAGG      360

CTAANCCCTA TNCTTTTAAA GGGCTNAAGG AACCAAACCT ATTTTAANCC TNTTNGTTTG      420

CNCCATGCAA AACTTTATGN AAAACCCCCA AACTAGGCTA TTTANCNNCT NCCATNAATG      480

GNCCCCAAAT CATNTNATNC TACGGCATAA ACAACANCTG CCCTATTTAC NCGGAACCTG      540

CAAANCTCAC AAGNAATGTG AATTNGCNCT NGGGANTCAA TGTTNCCGGG TNAATTATCT      600

TGGATNANAA CCNTTTTCTA CATNACTATT GAAAAAACCT GTGGTTTCTT GCTTTTTAAC      660

AAATNNGGTG TTCCTTTGCC CCCCCCCCTT ATTTTTCAAG GGCTGGGT                   708

(2) INFORMATION FOR SEQ ID NO: 35:

(i) SEQUENCE CHARACTERISTICS:
        (A) LENGTH: 675 base pairs
        (B) TYPE: nucleic acid
        (C) STRANDEDNESS: double
        (D) TOPOLOGY: linear (xi) SEQUENCE DESCRIPTION: SEQ ID NO: 35:

ATCACAGTCC AGAGAGTCCT AGAGGAGGAC GAGAGCATAA GANCTTGCCT TAGTGAAGAT       60

GCAAAAGAGA TTCAGAACAN AATAGAGGTA GAAGCAGATG GGCNAACAGA AGAGATTTTG      120

GATTCTCAAA ACTTAAATTC AAGAAGGAGC CCTGTCCCAG CTCAAATAGC TATAACTGTA      180

CCAAAGACNT GGAAGAAACC AAAAGATCGG ACCCGANCCA CTGAAGAGAT GTTAGAGGCA      240

GAATTGGAGC TTANAGCTGA AGAGGAGCTT TCCATTGACA AAGTACTTGA ATCTGANCAA      300

GATNTAATGA GCCAGGGGTT TCATCCTGAA AGAGACCCCT CTGACCTANA AAAAGTGAAA      360

GCTGTGGAAG AAAANTGGAGA ANAAGCTGAG CCAGTNCGTA NTGGTGCTGA GAGTGTCTCT    420

GAGGGTGAAG GANTAGATGC TACTTCAGGC TCCNCAGATA GTTCTGGTGA TGGGGTTACN     480

TNTCCATTTN AACCNGAATC CTGGAAGCCT ACTGATNCTG AAGGTNTGAN GCNNTNTGAC     540

NGGGAGTTCT GCTGGACTTC CAGTTCATGC CTGCCTGGTA TNCTTTNCCC GAGGGCCTGC     600

CTCCTNTCAG TGATTTGGTT CTTGACAAGA TCCNCCNTCC CCCTTTTGCC AATGCCGAAC     660

TCTGGGATCC TTCGA                                                      675

(2) INFORMATION FOR SEQ ID NO: 36:

(i) SEQUENCE CHARACTERISTICS:
        (A) LENGTH: 713 base pairs
        (B) TYPE: nucleic acid
        (C) STRANDEDNESS: double
        (D) TOPOLOGY: linear (xi) SEQUENCE DESCRIPTION: SEQ ID NO: 36:

GCTAAACATT TTTTAAGTA TGAGTCCTTG TTTAAAAAGA AAAGATTAAA ACAGAAAATA        60

TTTTCTATAA ATAATACATG TATTTTGGTT TTAGTGCTCC CGCCCTAAGG TTTGAAGTTT      120

ACTTTTATCC AGTACCTTTT TCCTCCATGA TCACCTTTTT TTCTCTTTCC CCTCTCCCAC      180

TCGTGCACAC GTGGGGTTT CTGCGAGAAT TGGCCTTGCT GCACTGTGAT TGGCGAANAC      240

GTGAAACTTT TTAAAAAAAT ACTTAAATTG TTTCTTTTGT TTCATTTTGT GTATTTGAAG     300

TTTTAGTTAT CCTCAGACTC CTCTTCTGCT TCCCGCAGCC ACGTGAAGAA TGCCGTGACA     360

GATTTCAGAG CCACGCCCTT CCCATTCTGC TCTGCAGGGT CCTTGCTGCT CTCCCATTTG    420

TAGAAGGCAT CCTCGGAGAT CACCTCCTCG TCATATAGAC AATCAAAAAA CATCCGCAGC    480
```

```
AAATTGGCAG GTTGATCAAG TTTTACTATC GATGCTTGTA GTGCATAAAG TGCTGCAGTT      540

CCTTCTCTGT ATCTGANTCT AGGTACTTGA GTAAGATCGG CACTCTCTGC TTGATAACAG      600

CAGTGTCCAC TCTGAAGGTA NAAGAATCNG GTTATTATAG CTTGCTTTAA CAAACAGCNG      660

TCNTTAAAGC TCTAAGGAAT GTTANGTGAA ATNCACTGGA TTTCGTCTAA ATT             713

(2) INFORMATION FOR SEQ ID NO: 37:

(i) SEQUENCE CHARACTERISTICS:
        (A) LENGTH: 554 base pairs
        (B) TYPE: nucleic acid
        (C) STRANDEDNESS: double
        (D) TOPOLOGY: linear (xi) SEQUENCE DESCRIPTION: SEQ ID NO: 37:

CATTCNAGAA AGATNTTACA CACGGAGTTT NCTCANTATT GGGCTCAACG GGAAGCTGAC       60

TTTACGGANA CTCTGCTTCA AGTAACGANA GATATTANAA GANAATGCTG GANCGTCGTT      120

TGGCTATCTT CNAGGATTTG GTTGGTAAAT GTGACCCTCG AGAANAAGCA GCGAAAGACA      180

TTTNTGCCAC CAAAGTTGAA ACTGAAGAAG CTACTGCTTG TTTAGAACTA ACTTTNATCC      240

AATTAAAGCT GAATTAGCTA AAACCAATGG AGAATTAATC TCNACCNCNC ACNANTTCNC      300

CCAGAGANAA NATGAATCCG ATTCATTGAT TCAAGAGCTT GAGACATCTG NTAAGANAAT      360

AATTNCACAN AATCTGGAGA ATTNNAGAAT TGATNAATAT NATTGATCNN TCGAAGATAC      420

TATCANCGAA TTTCAGAACC TNANGTCTCA TATGGAAAAC TCNTTTAAAT GCNATGACAA      480

GGCTGATACA TCTTCTTTAA TAATAAACAA TAAATTGATT TGTTATGAAA CAGTTGAAGT      540

ACCTAAGGGA CAGC                                                       554

(2) INFORMATION FOR SEQ ID NO: 38:

(i) SEQUENCE CHARACTERISTICS:
        (A) LENGTH: 551 base pairs
        (B) TYPE: nucleic acid
        (C) STRANDEDNESS: double
        (D) TOPOLOGY: linear (xi) SEQUENCE DESCRIPTION: SEQ ID NO: 38:

GACTGCATGT TCTCATTTAT TTATGGGATC TAAAAATAAA ATCAATTGAC CTCATGGGCA       60

TACANANTAA AAAAATGGTT ACCAGTGGCT GGTAAGGGTA CTGACGGTTG CAGGGGGAGG      120

TGGGGATGGT TAATGGGTAC AAAAACAAAT AAGATNAAAA GAATGATTTA ATATCTGATA      180

GCACAATANA NTGACTATAA TCAATAATAA CTTACTTGTA TATTTTTAAA TGATCTAAAA      240

AATGTAATTG GATTATCTGT AATTCAAAGG AAAAATGCTT GAGGGGATGG ATACCTCATT      300

CTCCATGATA CACGTNTTTC ACATTGATGC CTGTGTCAAA ACATCTCACA TACCCCGTAA      360

ATATATACAT GTACTATGTA CCACAAAATG TTTACAAAAT AAGTGANACA TTCTAATTAA      420

AGACTGAAAT CTTTTTCTAA ATAATGTATA TACATGTTTT GTGATCTGTA CACACTTATT      480

CTCCAAATCC TAACTNTANT CCCAACANAT ATNTTAAATC CTTGTTTANC NGAATAAGTT      540

AAAAAAATCC T                                                          551

(2) INFORMATION FOR SEQ ID NO: 39:

(i) SEQUENCE CHARACTERISTICS:
        (A) LENGTH: 680 base pairs
        (B) TYPE: nucleic acid
        (C) STRANDEDNESS: double
        (D) TOPOLOGY: linear
```

(xi) SEQUENCE DESCRIPTION: SEQ ID NO: 39:

| | | | | | |
|---|---|---|---|---|---|
| ATTTGGTAAC | AGGATTAAAA | AGAAATTTTT | AATTCCTTGT | CTCTCTTCTG | ATGGCTGAAC | 60
| AGAACTGCGG | TGTCAAATGG | AAAGCAGCAC | ACAAGAATTC | CCTTGCAGAC | CTTGATCTTT | 120
| CGCANAAATG | CAAAGACGCC | TGAGTTATAC | AACTTGCAAT | TATTATTTTC | TANACAGAAG | 180
| TGCCAACTGT | TGTGCTTTCC | AGTGTATCAG | TGGTTGCTAC | ATTCTCCTTC | TTGTCTTCGG | 240
| GTTTCATGGC | AGGAAACAGA | AGTACTTCCT | TGATGTTGTT | GGAGTCCGTG | AGAAACATGG | 300
| CGACTCGATC | AATGCCCATG | CCCCAGCCAG | CTGTGGGGGG | CAGCCCATAT | TCCAGGGCAG | 360
| TACAGAAGTT | TTCATCTATG | AACATGGCCT | CATCATCACC | TGCAGCCTTG | GCCTTGGCCT | 420
| GTTCTTCAAA | AANCTGCCGC | TGCCGCATGG | GATCATTCAG | CTCAGTATAC | GCATTGCATA | 480
| TCTCTTTCTT | CATGACAAAC | AGCTCAAANC | GCTCAGTCAG | ACCTCTTTAA | ANCGGTGCCA | 540
| TTTAACCNAA | GGGCCATTAT | CTGTGGGTGA | TCACAGATGA | ATGTNGGATT | GATGCAAGTC | 600
| ACTTCCANGA | ACTCCCCAAC | AANCTTGTCA | AGGAACCTGG | CTGTGGTCCA | ANGTGGAAGG | 660
| CATCCACANC | TTTTGCCCCC | | | | | 680

(2) INFORMATION FOR SEQ ID NO: 40:

(i) SEQUENCE CHARACTERISTICS:
        (A) LENGTH: 753 base pairs
        (B) TYPE: nucleic acid
        (C) STRANDEDNESS: double
        (D) TOPOLOGY: linear (xi) SEQUENCE DESCRIPTION: SEQ ID NO: 40:

| | | | | | |
|---|---|---|---|---|---|
| ACAAATATGA | ACGTCTGAAG | GCAAACCAGG | TAGCTACTGG | CATTCGGTAC | AATGAAAGGA | 60
| AAGGAAGGTC | TGAACTAATT | GTCGTGGAAN | AAGGAAGTGA | ACCCTCAGAA | CTTATAAAGG | 120
| TCTTAGGGGA | AAAGCCAGAG | CTTCCAGATG | GAGGTGATGA | TGATGACATT | ATANCAGACA | 180
| TAAGTAACAG | GAAAATGGCT | AAACTATACA | TGGTTTCAGA | TGCAAGTGGC | TCCATGAGAG | 240
| TGACTGTGGT | GGCANAAGAA | AACCCCTTCT | CANTGGCAAT | GCTGCTGTCT | GAAGAATGCT | 300
| TTATTTTGGA | CCACGGGGCT | GCCAAACAAA | TTTTCGTATG | GAAAGGTAAA | GATGCTAATC | 360
| CCCAAGAGAG | GAAGGCTGCA | ATGAAGACAG | CTGAAGAATT | TCTACAGCAA | ATGAATTATT | 420
| CCAAGAATAC | CCAAATTCAA | GTTCTTCCAG | AAGGAGGTGA | ACACCAATC | TTCAAACAGT | 480
| TTTTTAAGGA | CTGGAGAGAT | NAACGATCAG | AGTGATGGCT | TCGGGAAAGT | TTATGTCACA | 540
| GAGAAAGTGG | CTCAANTNNA | ACNAATTCCC | TTTGATGCCT | CNNAATTACN | CAGTTCTCCG | 600
| CAGATGGCAG | CCCAGCACAA | TATGGTGGAT | GATGGTTCTG | GCCAAGTGGA | AATTTGGCGT | 660
| GTNCAAAACA | ATGGTAGGAT | CCAAGTTGAC | CNNAACTCCT | ATGGTGACTC | CCATGGTGGT | 720
| ACTGCTACT | TCATACTCTA | CACCTATCCC | TGA | | | 753

(2) INFORMATION FOR SEQ ID NO: 41:

(i) SEQUENCE CHARACTERISTICS:
        (A) LENGTH: 675 base pairs
        (B) TYPE: nucleic acid
        (C) STRANDEDNESS: double
        (D) TOPOLOGY: linear (xi) SEQUENCE DESCRIPTION: SEQ ID NO: 41:

| | | | | | |
|---|---|---|---|---|---|
| GGTGTTTCCA | AAGGCTTTTA | ATAAGGTTAA | AAAAAAAATA | AAATNCCNCT | TAAAAAATAA | 60
| CNCTTANCAN | TTAATGACAT | CAAANTCNCN | TTGACTAAAA | AAGGAAAATA | NCAACCAATT | 120

```
GTTAAANCCA CCTTAACATA AACCTTATNG CAATTNTACA CNTCTTTTGA ACNCAATCTA        180

TAAAAAAAAA AATAACTNCC ANGGCATTAC AACTTTTNCT CTGGCATNTT AAAAAACAAC        240

TCTNACTAAT GGCTAATGCA TTATAAAATT NCCTATCTNA CAAATCTTNC TAAATTATGC        300

ATAGTATTTT ACTTTTNAAA GGTCNTAAAA AAAATATAAA TCANTTNCCA TAAAANCTAA        360

TATNGGCCCA TAACAAAANT TCCCTNCAGG TTATTTTAAT NTNTTAACNT AAAAAAACNC        420

CAGNTGAAAA AAAATTNCAA NCCAAAACTA ACCNTTAAAA AATAGGCNTT NGGTTNAGGT        480

TAATTTTTTT TTTTTTTTTT TTGNAAANAA ANTCNCTNTT GCCCAGNCTG GATTGTGGTG        540

GCNCCAATCC TGGCTCACTG CAACCTCAGC CTCCTGGGTT CAAGCAATTT NCCTGTCTCA        600

GCCTTCCAAN TTCCNGGGAA TACAGGGGTN CNCCACCACN CCCAGCTAAA TTTTTTTTGT        660

TTTTTTTANT AAAAG                                                         675

(2) INFORMATION FOR SEQ ID NO: 42:

(i) SEQUENCE CHARACTERISTICS:
        (A) LENGTH: 677 base pairs
        (B) TYPE: nucleic acid
        (C) STRANDEDNESS: double
        (D) TOPOLOGY: linear (xi) SEQUENCE DESCRIPTION: SEQ ID NO: 42:

AAGATCAGCG ATATCACGCG TCCCCCGGAG CATCGCGTGC AGGAGCCATG GCGCGGGAGC         60

TATACCACGA AGAGTTCGCC CGGGCGGGCA AGCAGGCGGG GCTGCAGGTC TGGAGGATTG        120

AGAAGCTGGA GCTGGTGCCC GTGCCCCAGA GCGCTCACGG CGACTTCTAC GTCGGGGATG        180

CCTACCTGGT GCTGCACACG GCCAAGACGA GCCGAGGCTT CACCTACCAC CTGCACTTCT        240

GGCTCGGAAA GGAGTGTTCC CAGGATGAAA GCACAGCTGC TGCCATCTTC ACTGTTCAGA        300

TGGATGACTA TTTGGGTGGC AAGCCAGTGC AGAATAGAGA ACTTCAAGGA TATGAGTCTA        360

ATGACTTTGT TAGCTATTTC AAAGGCGGTC TGAAATACAA GGCTGGAGGC GTGGCATCTG        420

GATTAAATCA TGTTCTTACG AACGACCTGA CAGCCAAGAN GCTCCTACAT GTGAAGGGTC        480

GTANAGTGGT GAGAGCCACA GAATTCCCCT TAGCTGGGAC AGTTTCAACA AGGGTGACTG        540

CTTCATCATT GACCTTGGCA CCGAAATTTA TCANTTGGTG TGGTTCCTCN TGCAACAAAT        600

ATGAACGTCT GAAGGCAAAC CANGTANCTA CTGGCATTCG GTNCAATGAA AGGAAAGGAA        660

GGTCTGAACT AATTGTC                                                       677

(2) INFORMATION FOR SEQ ID NO: 43:

(i) SEQUENCE CHARACTERISTICS:
        (A) LENGTH: 665 base pairs
        (B) TYPE: nucleic acid
        (C) STRANDEDNESS: double
        (D) TOPOLOGY: linear (xi) SEQUENCE DESCRIPTION: SEQ ID NO: 43:

GAGACAGAGT CTCTGTTGCC CAGGCTGGAG TGTGGTGGCG CAATCCTGGC TCACTGCAAC         60

CTCAGCCTCC TGGGTTCAAG CAATTTTCCT GTCTCAGCCT TCCAAGTAGC AGGGACTACA        120

GGCGTGCACC ACCACGCGCA GCTAATTTTT TTGTATTTTT AGTAAAGGCG AGGTTTCGCC        180

ATGTTGGCCA GGCTGGTCTC GAAATCCTGA CCCCAGTGAT CTGCCTACCT CATCCTCTCA        240

AAGTGCTGGG ATTACAGGTG TGAGCCACCG CGCCCAGCCT TAATTTTCAA AAGACAAATA        300

AGCAAAAAGC TTTTCCCGTT CCTCTCCCAA AACAGCAATG AGATAACTGC CTTGTAATGT        360

TTGTTTGCTT TTTACAAATA CCAATTTACC ACTTGCTGGA ATCCCAGCCC AGGAACCAGC        420
```

```
CTGTGAATGT GGGTGGCTCA TGGCCCTGTT TTATGATGAC AATTGGTGTC CTCTTGTCTC      480

TTCCAGAAGG GTCTGTCTCA AGGTACATTT TGGCANACTT CAAAGATTCT TTTTTCTCAA      540

CTTCATTAGC ATCTTTGCCA ATCCAAATAA ATATCTGTTC CCAAGCATCT AGTAACATGA      600

CATCATCTTC AGCTAAATCA TCCTGGGTGA ACTCTCCCTG GAATCTCTTC AATAACAAAT      660

CTCCC                                                                  665

(2) INFORMATION FOR SEQ ID NO: 44:

(i) SEQUENCE CHARACTERISTICS:
          (A) LENGTH: 698 base pairs
          (B) TYPE: nucleic acid
          (C) STRANDEDNESS: double
          (D) TOPOLOGY: linear (xi) SEQUENCE DESCRIPTION: SEQ ID NO: 44:

CTGAGGAGCT GGTGGTCTTT GAGGATTTGA ATGTATTTCA CTGCCAGGAA GAATGTGTGA       60

GCTTGGATCC TACTCAACAA CTCACGTCAG AGAAGGAAGA TGACAGCAGT GTCGGGAAA       120

TGATGTTACT GGTCAATGGC AGTAATCCTG AAGGTGAAGA TCCTGAGAGG GAACCTGTAN     180

AAAATGAAGA TTATAGAGAA AAGTCTTCAG ATGATGATGA AATGGATTCT TCCTTGGTCT     240

CTCAGCAGCC TCCCGATAAC CAGGAAAAGG AACGACTAAA TACATCCATT CCACAAAAAA     300

GGAAAATGAG AAATCTGTTA GTTACCATTG AGAATGATAC TCCTCTAGAG GAACTCTCAA     360

AATATGTAGA CATCANTATT ATTGCCCTTA CTCGAAATCG GAGGACAAGG AGATGGTACA     420

CTTGTCCACT GTGTGGGAAA CAGTTTAATG AAAGTTCTTA CCTCATTTCC CACCAGAGGA     480

CCCACACTGG AGAAAAACCC TATGACTGTN NTCACTGTGG GAAAAGCTTC AATCATNAAA     540

CAAACCTCAA TAAACATGAG CGAATTCNTA CAGGAGAGAA ACCTTATTCC TGTTCTCAGT     600

GTGGAAAAAA CTTCCGTCNG AATTCTCATC GGAGTCGTCC TGAAGGAATC CATNTAACGG     660

AGAAGATATT AAGTGTCCAN AATGTGGGAA AACCTCCC                             698

(2) INFORMATION FOR SEQ ID NO: 45:

(i) SEQUENCE CHARACTERISTICS:
          (A) LENGTH: 466 base pairs
          (B) TYPE: nucleic acid
          (C) STRANDEDNESS: double
          (D) TOPOLOGY: linear (xi) SEQUENCE DESCRIPTION: SEQ ID NO: 45:

ATCACAAATT GTAAATATTA TTGAAATTGA TTGCAAATTT AGATCACATA CAAATGAGAG       60

TCTGACATTC AACTGTTTTC CTATATTCCA AAGTAAACAA TTCCTTTCAA CACTCAAGAC     120

TTAAACAGGT ATTCTTAGAG GGTTATATGA ATTGCTATCA GAAGCTGTTG GCTAACAAGC     180

CAGTAATTTG GTTCTTTCAC CANAACACAG TTCCAGATAA GCATCTTTGC ACTATTTCTC     240

AANTATGAAT CCCCATGTGG GGGGAAAACG GATATACTTT CAATAGACAC AAGTCACTCT     300

TTGCCTTCCA AGTAAGCANA CTCCAGATTC ATCTTCAAAG TGTTGGGAAA NGGGATCTGT     360

GACCTGTNCA TTATCATATA ACTTCAAAAA GGAAAGCTCC TTANTCCAAA AAGCCTANAT     420

GCTGAGGTAT AGCCCTTGAA ATGTTTTCTT CCCTGTNAAT TTCCTA                    466

(2) INFORMATION FOR SEQ ID NO: 46:

(i) SEQUENCE CHARACTERISTICS:
          (A) LENGTH: 734 base pairs
          (B) TYPE: nucleic acid
```

(C) STRANDEDNESS: double
        (D) TOPOLOGY: linear (xi) SEQUENCE DESCRIPTION: SEQ ID NO: 46:

CACATACAGT CTTTGTTTTA ATGTTTATTG GTAGAAACAG ATCTTCAATG CATACTTTGT      60

GTTTATATAA ACTCTACATT CTCTTAAAGG TTTTCGTTTT GTTTTCACTG GAGATTTTTA     120

GCCTCCAAGT GAACTTAACA TATTGCCTAT GCATCTGATT CTTTATANAC TTTTANATTT     180

TAAAACTAAA TTTGANAAAC CATGCATACT GTATACCTTA TTTAATAATC CAAANAATTG     240

TTTGCACTTT CAAAAAAGTT ACAAAAAGGC TGAACACAAG TTAAATAACC TATATGATGT     300

AAATTTTCCA TTTCTGAATA CTTTTTCAGT ATTATATATT GCTTGCTGTC TAATAAGTTA     360

GATTGTCAGA NACGCTTCAG TAAATTATCT CTACTTTAAA ATTATATCTG AATCCCCTTT     420

CTCTGANATG AACTTGCCAA TATTAAACAT TGTGCCATAT GCAGTATTAN CCCAAAAGCT     480

TAAATAAGAA CCAAACTTGT AGACTGAATA TTTTAACCTT AAAATTATAT ACCTATATAT     540

NCACCTATGG TATGCTGCAT ATTAAATTTA ACATTTCAAG TAACATATAT ATAGCAAACA     600

TTCAGCCAAA TACTCTTTCA TGAAAAGATA CTGTCCTTAA AATAAAAAGT TANTGAAAAG     660

CTTATTTAGA CCNAATGTCT AAATATAANT NCTAAGCCTA TGAAACTTGA ANCTAAAGTC     720

TGCTGTNCTA TTTA                                                      734

(2) INFORMATION FOR SEQ ID NO: 47:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (xi) SEQUENCE DESCRIPTION: SEQ ID NO: 47:

CTCCTGTGCT TACACCTGTA GAAAACACC AGAGCAGAGA GTATCTCAAG TGATGAAGAG       60

GTTCATGAAT CTGTGGATTC AGACAATCAG CAAAATAAAA AAGTTGAAGG TGGATATGAA     120

TGTAAATATT GTACTTTTCA AACTCCAGAT CTAAATATGT TTACTTTTCA TGTGGATTCG     180

GAACATCCCA ATGTAGTGCT AAATTCATCC TATGTTTGTG TCGAATGCAA TTTTCTTACC     240

AAAAGGTATG ATGCACTTTC TGAGCATAAT CTGAAATATC ACCCAGGAGA AGAGAATTTT     300

AAGTTGACTA TGGTGAAACG TAATAACCAG ACAATCTTTG AACAAACAAT AAATGATCTG     360

ACTTTTGATG GTAGTTTTGT TAAAGAGGAG AATGCAGAGC AAGCAGAATC TACAGAAGTT     420

TCTTCTTCGG GAATATCTAT CAGTAAAAACT CCTATCATGA AAATGATGAA AAATAAAGTG    480

GAAAATAAAC GGATTGCAGT TCATCATAAC TCAGTTGAGG ACGTTCCTGA AGAGAAAGAG     540

AATGAAATCA AACCAGACCG TGAAGAAATT GTAGAAAATC CAAGTTCTTC AGCTTCTGAA     600

TCTAATACAA GTACTTCCAT TGTAAACAGA ATACATCCAA GTACTGCCAG CACGGTAGTG     660

ACCCAGCAGC AGTTCCTCCC TGGATTGGGC CCAGGTGATA ACTGCTGTNT CTGCTCCGCC     720

AGAATTCTAA TTTGATTCCC NAAGTCTTAA TCCCTGTTNA TANCATCCCC CCTACAATGC     780

TGCNTTGGAT AACAACCCCC TTTTTACTTA ACCCCTACAN CC                       822

(2) INFORMATION FOR SEQ ID NO: 48:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (xi) SEQUENCE DESCRIPTION: SEQ ID NO: 48:

```
ACCCATTTCT AACAATTTTT ACTGTAAAAT TTTTGGTCAA AGTTCTAAGC TTAATCACAT      60
CTCAAAGAAT AGAGGCAATA TATAGCCCAT CTTACTAGAC ATACAGTATT AAACTGGACT     120
GAATATGAGG ACAAGCTCTA GTGGTCATTA AACCCCCTCA GAAAGTCTAA GATTCAGAAT     180
GTCTCCATCA TATTAGAAGA AAAATGTACT GTATTAAAAT TTAAATTGCA TTTTTACAAG     240
TTGTTTTTTA ATTAGTGTTC TATTTACATT GCANAACTTC CACCAACTGC AGTAGTTTAA     300
CTTTGGCACA ACATTAAGTT CCATTTCTTT TGGGTATTGG ATCCTGCTTT TTGAGTGTGT     360
ATGCCCCAAA ACGTTTTCAA TGTCATCAAA GATTGGGCAA ATTCACAGTA AATCAGACAT     420
CTTGAGTTGA AGAATTGATT CTCCTTCAAC GTTTTAGGCA GATTTCAGTC ATCTGATTTA     480
GACAGCTTCC GTTTCACATG TCGTGGAAGT CCCAAGTGTC ACTATCATCT GTTTCTTCTT     540
CATCCTCTTC CTGGTCATCA ATAACTTCAT CTTCCTCCTC ATTTTCCTCA AATAATTCTA     600
TACCTAATTC TGATCTTCTC TGTCTTTCTG CAAACCACTC TCTGACCTGC TCATANCCCA     660
TATGTGATTT GTTAACAAAT TCATCAAGGT CTTGCTCATT AAAAAACTTG TGCTTCAGGT     720
TATAATCCTT AANTTTTGCC GTTCCAGTTT TAAATTTTAT GAATNAATGG TCCCCTGGTC     780
CCCAGTTGTT AATTCCTTTT GGCTCCTCCA AGGCGCCCA                            819
```

(2) INFORMATION FOR SEQ ID NO: 49:

(i) SEQUENCE CHARACTERISTICS:
        (A) LENGTH: 704 base pairs
        (B) TYPE: nucleic acid
        (C) STRANDEDNESS: double
        (D) TOPOLOGY: linear (xi) SEQUENCE DESCRIPTION: SEQ ID NO: 49:

```
AAAAAGTTAT TTATTTATTC TTTTTTTTTT TTTTTTTTTT TTGGTAAGGT TGAATGCACT      60
TTTGGTTTTT GGTCATGTTC GGTTGGTCAA ANATAAAAAC TAANTTTGAN ANATGAATGC     120
AAAGGAAAAA AATATTTTCC AAANTCCATG TGAAATTGTC TCCCATTTTT TGGCTTTTGG     180
GGGGGTTCAG TTTGGGTTGC TTGTCTGTTT CCGGGTTGGG GGGAAAGTTG GTTGGGTGGG     240
AGGGANCCAG GTTGGGATGG AGGGAGTTTA CAGGAAGCAN ACAGGGCCAA CGTCNAAGCC     300
NAATTCCTGG TCTGGGCAC CAACGTCCAA GGGGGCCACA TCNATNATGG GCAGGCGGGA     360
GGTCTTGGTG GTTTTGTATT CAATCACTGT CTTGCCCCAG GCTCCGGTGT GACTCGTGCA     420
NCCATCGACA GTGACGCTGT AGGTGAANCG GCTGTTGCCC TCGGCGCGGA TCTCGATCTC     480
GTTGGAACCC TGGAGGANCA GGGCCTTCTT GAGGTTGCCA GTCTGCTGGT CCATGTAGGC     540
CACGCTGTTC TTGCANTGGT ANGTGATGTT CTGGGAGCCT CGGTGGACAT CAGGCGCAGG     600
AAGGTCACCT GGATGCCACA TCNGCANGGT CGGAACCCTG GCCGCCATAC CCCAACTGGG     660
AATCCATCNG TCATGCTCTC CCCGAAACAA AACATCCTCT TGTT                     704
```

(2) INFORMATION FOR SEQ ID NO: 50:

(i) SEQUENCE CHARACTERISTICS:
        (A) LENGTH: 693 base pairs
        (B) TYPE: nucleic acid
        (C) STRANDEDNESS: double
        (D) TOPOLOGY: linear (xi) SEQUENCE DESCRIPTION: SEQ ID NO: 50:

```
GAAAGCAAAT TTCTTTTAAT GANAACTCAA AATTAAACTT CAAAGGGACC CAACGTCATA      60
CTTCCATTCA GGGACTTGAT ACAAAAAATT TAGTTTGAAC TGCTATTAGC AGGTGGCAGG     120
```

```
AGCCACCTTC AAATGAATCT TCAAATTGGA AAATACTGCT TCACCACCTG TTGGGGATAA      180

NTTGCAAATG GAATAATTTA GTATGGTTTG TAGCTATTTT GATNACCACC TCGCCTGNAT      240

ACCTTCCCAT AACCACTCTG CTGGTCACCA CCTCTTCCAC AAGCTCTTCC TGCAAATCCT      300

CCTCTAAATC CCCACTGTTG CTGTTGCTGA TATTGTNCCT TCGACATGGC TACTTTTATT      360

TCACATTTAC TAAAACCAAC ATTGTGGTAT TTCTTTTCCA TTATCTTCTT CACTGGTTCT      420

TCTTCCTTAA AGGTAATAAA GCAAAACCCA CGCCTCTTAT TGGTCTTGTT GTCCATGGGG      480

AGCTCTATGG ATTCCACCTC ACCAAAACCA CCAAAGTACT CCCTTATTTT CTCTTCAGGT      540

GTATCTGGAN AAAGGCCACC ANCNAAAATT TTTTAACCGG CTCTTTTGTT TCCATGGCTT      600

TGGGCCTTTT ANGATCAATC ACCTTCCCCA TTCAATTTAT GTTCTTTTTG GATCCATGAA      660

CCTTTNTCTA CNCCCTCCCG AATTCCTTAA ATA                                  693

(2) INFORMATION FOR SEQ ID NO: 51:

(i) SEQUENCE CHARACTERISTICS:
        (A) LENGTH: 619 base pairs
        (B) TYPE: nucleic acid
        (C) STRANDEDNESS: double
        (D) TOPOLOGY: linear (xi) SEQUENCE DESCRIPTION: SEQ ID NO: 51:

GCACTCTGAA GTTAGATCCT ATCACAGGGC GATCAAGGGG TTTTGGCTTT GTGCTATTTA       60

AAGAATCGGA GAGTGTANAT AAGGTCATGG ATCAAAAAGA ACATAAATTG AATGGGAAGG      120

TGATTGATCC TAAAAGGGCC AAAGCCATGA AAACAAAAGA GCCGGTTAAA AAATTTTTGT      180

TGGTGGCCTT TCTCCAGATA CACCTGAAGA GAAAATAAGG GAGTACTTTG GTGGTTTTGG      240

TGAGGTGGAA TCCATAGAGC TCCCCATGGA CAACAAGACC AATAAGAGGC GTGGGTTCTG      300

CTTTATTACC TTTAAGGAAG AAGAACCAGT GAAGAAGATA ATGGAAAAGA AATACCACAA      360

TGTTGGTCTT AGTAAATGTG AAATAAAAGT AGCCATGTCG AAGGAACAAT ATCAGCAACA      420

GCAACAGTGG GGATCTANAG GAGGATTTGC ANGAAGAGCT CGTGGAAGAN GTGGTGGCCC      480

CACTCAAAAC TGGAACCANG GATATANTNA CTATTGGAAT CNAGGCTATG GCAACTATGG      540

ATATNACAGC CCAGGTTACC GTGGTTNTGG AAGATATGAC TNCACTGGTT ACNACAACTA      600

CTATGGATAT GGTGATTAT                                                  619

(2) INFORMATION FOR SEQ ID NO: 52:

(i) SEQUENCE CHARACTERISTICS:
        (A) LENGTH: 694 base pairs
        (B) TYPE: nucleic acid
        (C) STRANDEDNESS: double
        (D) TOPOLOGY: linear (xi) SEQUENCE DESCRIPTION: SEQ ID NO: 52:

CGGCGGCGCC ATTAAAGCGA GGAGGANGCG AGAGCGGCCG CCGCTGGTGC TTATTCTTTT       60

TTAGTGCAGC GGGAGAGAGC GGGAGTGTGC GCCGCGCGAG AGTGGGAGGC GAAGGGGGCA      120

NGCCAGGGAN AGGCGCAGGA GCCTTTGCAG CCACGCGCGC GCCTTCCCTG TCTTGTGTGC      180

TTCGCGAGGT ACAGCGGGCG CGCGGCANCG GCGGGGATTA CTTTGCTGCT AGTTTCGGTT      240

CGCGGCAGCG GCGGGTGTAT TCTCGGCGGC AGCGGCGGAG ACACTATCAC TATGTCGGAG      300

GANCANTTCG GCGGGGACGG GGCGGCGGCA NCGGCAACGG CGGCGGTAGG CGGCTCGGCG      360

GGCGAACANG ANGGANCCAT GGTGGCGGCG ACACANGGGG CANCGGCGGC GGCGGGAACN      420
```

```
GACCGGGACC GGGGGCGGAA CCGCNTCTGG ANGCTCCNAA GGGGGCNNCG CCNAATCCGA    480

AGGGGCGAAA ATTGACCCCG TATGAACCAA GAAGATGAAT GGAAAATGTT TATANGAAGC    540

CTTANCTGGG ACACTNCCCA GAAAGATCTG AAGGACTACT TTTCCNAATT TTGGGTGAAA    600

TTGTTAAACT GCCCTCTTGA AATTTTNATN CTATCCCNGG GGCNATCAAA GGGGTTTTTG    660

GCTTTTTTCC TATTTTAAAC AAATCCCGAA AAAT                                 694
```

(2) INFORMATION FOR SEQ ID NO: 53:

(i) SEQUENCE CHARACTERISTICS:
        (A) LENGTH: 728 base pairs
        (B) TYPE: nucleic acid
        (C) STRANDEDNESS: double
        (D) TOPOLOGY: linear (xi) SEQUENCE DESCRIPTION: SEQ ID NO: 53:

```
CGCCACTGCN GCAGGAGGCG TGAGGGGATA AAAACATTCA GATGGCAGAT CACAGTTTTT     60

CAGATGGGGT TCCTTCAGAT TCCGTGGAAG CTGCTAAAAA TGCAAGTAAC ACAGAAAAGC    120

TCACAGATCA GGTGATGCAG AATCCTCGAG TTCTGGCAGC TTTACAGGAG CGACTTGACA    180

ATGTCCCTCA CACCCCTTCC AGCTACATCG AAACTTTACC TAAAGCAGTA AAAAGAAGAA    240

TTAATGCATT GAAACAACTT CAGGTGAGAT GTGCTCACAT AGAAGCCAAG TTCTATGAAG    300

AGGTACATGA CTTGGAAAGA AAGTATGCAG CGCTATACCA GCCTCTCTTT GACAAGAGAA    360

GAGAATTTAT CACCGGCGAT GCTGAACCAA CAGATGCGGA ATCGGAATGG CACAGTGAAA    420

ATGAAGAGGA AGAGAAATTG GCTGGAGACA TGAAAAGTAA AGTAGTCGTC ACAGAAAAAG    480

CAGCGGCAAC GGCTGAAGAG CCAGATCCCA NAGGAATTCC AGAGTTCTGG TTTACCATCT    540

TCAGAAATGT GGACATGCTG AGTGAATTAN TCCAGGAAAT ATGATGAACC AATCTTGAAA    600

ACACCTGCAG GATNTTAAAG TTGAAATTTT CTGACCCTGG ACAGCCTATG TCTTTTGTGT    660

TAGAATTCCA CTTTGAACCC CACGACTACT TTACCAACTC AGTCCTGACA AAAACCTTAC    720

CAGATGAA                                                             728
```

(2) INFORMATION FOR SEQ ID NO: 54:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (xi) SEQUENCE DESCRIPTION: SEQ ID NO: 54:

```
ACCTAATTAG ATAGAAGTTC AGGAATTTCT ATTTCTTTTG GGTTGATGAA CCACAGGCTA     60

GCATAAGTCC ACTGTCAATA AATGTTTGTT GTGGCCAGAC CTCCATAAAA GAGATATTCC    120

CTGTGTTCAC AAGTTCCCTG AAGCTTAGGT TTTGAGAGAA TATTGTTGAG TCACTAGGCA    180

GGGCTCACAT AGGAAACTGG CAATCACCTC TGAAACTGCT TCACAGACAC CTGCTTTTCC    240

TGCTCTGTTC CTCANACTTC TCCTCTTCAA GCGTATTCCC CCCACAACAA GGACAGCAGC    300

TTGGACTACA TATCTGGCTG ATGATGTAAT AAAAAGATTA GGCATGGGGG TTTCCTAAGC    360

CACAATTCAG GGCCACTCTG CACCAACAGA GATAAGCACC CAGGTGGAAG CCCCCCTTCC    420

CCGAGCCTCA TACATTGTCA TCATCTTCTA TGGCCTCCCC AGTGAAGTAC AGCACAGCCC    480

GCGGGACTAT CCGCTCACGG AAAAAGTGTC CAATTTCAAA ATCAGAAGCT AATGTGAATT    540

CAAAATCTTC ATCCAGTGAT CTCCATCCCC GGATGCTTTC CAATGGATTG AAGAAATTGA    600

AAAAGGACTC ATTGGGTACT GTTTCGTAAT TGTTCTAACA GTGCCTCAAC CTTATGCTTC    660
```

```
TGCTTTNCNT GGAAGGTNTT GAAAGTAACA TTCTTNCCTT CTTCCAANTC AATTATTNAC      720

CCCCGTTCAC AA                                                         732

(2) INFORMATION FOR SEQ ID NO: 55:

(i) SEQUENCE CHARACTERISTICS:
        (A) LENGTH: 582 base pairs
        (B) TYPE: nucleic acid
        (C) STRANDEDNESS: double
        (D) TOPOLOGY: linear (xi) SEQUENCE DESCRIPTION: SEQ ID NO: 55:

GCTTTTCTTC TTCCTCCTCT TCTGATTCTG GCTCTTGCTT TATTTGTGGC TGCCTGCGCC       60

TCTCAGCCTC TTGTTCCATC CTCTGGAGCT CTGCATCTGG ATCTGGATGC CCTTCTGCCA      120

NAAGGCGCTG CCTGATTTCC TCAAGCTCCT CCTTCTCTCT CTTCCTATCT CGTTCATCTG      180

CTTCCATTTC CTTTTCTCTA TCACGCAACC TTTTCTGAAA AGCACTTCCT CTGTAATATT      240

TGGGGTCATC TCTATCATCA TCATAGTCTT CTAANAATTC TTTTAGTCGT TTAGCTTCTT      300

TGGCCATTTC TCTTCTTCTT TCTTCTTCTC TTTCAGCTTC TTTCTCATAT TCCCGGGTTT      360

TCTTTCGTTC TCTGATTTCC CAATTCTTAA GGCGCTCTTG ATAANCAGCT TCTTTCTCTC      420

GGANTTTTCT TTCAAGTTTT CTTCGTTCGT ATGCATCTTC TTCATCTTCT TCTCGGTCCC      480

GTTTTTTGTC TTTTTCTCTT TCTCGCTCCC GTTCCTCTCT CNCTCTCTCT CTCGCTCCCG      540

TTCTCGTTCT CGCTCTCNTT CTCTCTCTCT CTCTCTTTCC CG                        582

(2) INFORMATION FOR SEQ ID NO: 56:

(i) SEQUENCE CHARACTERISTICS:
        (A) LENGTH: 784 base pairs
        (B) TYPE: nucleic acid
        (C) STRANDEDNESS: double
        (D) TOPOLOGY: linear (xi) SEQUENCE DESCRIPTION: SEQ ID NO: 56:

AAGAAAAGCT CAAGTTTCCA AGTCTCTTAA GGGAGCGATT AGGCATGTCA GCTGATCCAG       60

ATAATGAGGA TGCAACAGAT AAAGTTAATA AAGTTGGTGA GATCCATGTG AAGACATTAG      120

AAGAAATTCT TCTTGAAAGA GCCAGTCAGA AACGTGGAGA ATTGCAAACT AAACTCAAGA      180

CAGAAGGACC TTCAAAAACT GATGATTCTA CTTCAGGGAG CAAGAAGCTC CTCCACTATC      240

CGTATCAAAA CCTTCTCTGA GGTCCTGGCT GAAAAAAAAC ATCGGCAGCA GGGAAGCAGA      300

GAGACNAAAA AGCNAAAAGG GATACAACTT GCATCAAGCT AAAGATTGAT AGTGAAATTA      360

AAAAAACAGT AGTTTTGCCA CCCATTGTTG CCAGCAGAGG ACAATCAGAG GAGCCTGCAG      420

GTAAAACAAA GTCTATGCAG GGAGGTGCAC ATCAAGACGC TGGAAGANAT TAAACTGGAG      480

ANGGCACTGA GGGTGCAGCA GAGCTCTGAG AGCAGCACCA GCTCCCCGTC TCAACACGAG      540

GCCACTCCAG GGGGCNAGGC GGCTGCTGCG AATCACCNNN AGAACCGGGA TGAAAGAAGA      600

GAAGANCCTT CCGGGAAGGG AATGAAGTTG ATTCTCAGAG CNGTATTAGA ACNGAAGCTA      660

AAGANGCTCC GGGTGAGAAC NCCGGGGTTG ACCTCCCTAA AATTCCAGTC CAGAGATGTN      720

AGACCTGAAA GAGAACCCCT GCCGANACCG CCGGGAAAGG GANAAATCCG TCTTGACCCC      780

CTTC                                                                  784

(2) INFORMATION FOR SEQ ID NO: 57:

(i) SEQUENCE CHARACTERISTICS:
```

(A) LENGTH: 749 base pairs
    (B) TYPE: nucleic acid
    (C) STRANDEDNESS: double
    (D) TOPOLOGY: linear (xi) SEQUENCE DESCRIPTION: SEQ ID NO: 57:

| | | | | | |
|---|---|---|---|---|---|
| CCTACATCAG | TTTTATTTAA | AACACAAACA | AGTATTTCTC | TTTCTGTAAG | GGCAAATGGT | 60 |
| TCAAATAATG | CGGAACACGA | AACATTGACT | AATACAAGTG | CTTTAAATAT | GAAACAAAAT | 120 |
| TATTTTTTAA | AAAAGCAAAA | NAATAAAGAA | TATATACAAA | AGGGACCTGN | AATCTGTAAG | 180 |
| GTGATTCCAA | AAACNAAATA | ANTAGAAAAT | CCATGGTGAA | ACCTGAACAT | TCTACCTCTG | 240 |
| CTTTGGAGAA | GGGCTATCAT | ACAACATTCA | GTCAGCTGAA | NATGGATTGG | TANAGGTGTG | 300 |
| TCTATACATA | AACTTCAGTC | ATTTTTGCTT | GTGCANAATC | ATCCCAATCT | TCCCAANACT | 360 |
| GAATGGGCAG | TCCTGTGGCT | TTCTTCCTTT | TCCATATTCC | CAACAAGGCT | ACGTGAAGTT | 420 |
| CAACTCTTGA | TGAGCCGCTT | ACAACAGCAG | TTCCTTAGGG | AGCCAACATG | ACAGGTGGGT | 480 |
| CANATTTCCC | TATGAGAAAC | AAAACTGGCC | ACCTACAGCA | AAATATCAAA | ATGGGTAAGT | 540 |
| CCTTCCTTCC | TCTTCCTCCT | GATTATATAC | AACATATCTC | CTTTCAAGAC | TATTATTTCC | 600 |
| ATCATGCTTA | TTCCTTCACA | AATCTAAACC | TTGAGGTGAT | ATGAAGGAAA | CCANCNTCAA | 660 |
| AAAAAAGAAA | ACTCAATTCC | GAAATGAANA | AAACTGGGCN | NGGTATNCAA | TACNCCCCAN | 720 |
| AACATCTCCA | TATCCCTGGC | CCAGTTACC | | | | 749 |

(2) INFORMATION FOR SEQ ID NO: 58:

(i) SEQUENCE CHARACTERISTICS:
        (A) LENGTH: 751 base pairs
        (B) TYPE: nucleic acid
        (C) STRANDEDNESS: double
        (D) TOPOLOGY: linear (xi) SEQUENCE DESCRIPTION: SEQ ID NO: 58:

| | | | | | |
|---|---|---|---|---|---|
| AGACTTTCCT | ACATCAGTTT | TATTTAAAAC | ACAAACAAGT | ATTTCTCTTT | CTGTAAGGGC | 60 |
| AAATGGTTCA | ATAATGCGG | AACACGAAAC | ATTGACTAAT | ACAAGTGCTT | TAAATATGAA | 120 |
| ACAAAATTAT | TTTTTAAAAA | AGCAAAGAA | TAAAGAATAT | ATACAAAAGG | GACCTGGAAT | 180 |
| CTGTAAGGTG | ATTCCAAAAA | CGAAATAAGT | AGAAAATCCA | TGGTGAAACC | TGAACATTCT | 240 |
| ACCTCTGCTT | TGGAGAAGGG | CTATCATACA | ACATTCAGTC | AGCTGAAGAT | GGATTGGTAG | 300 |
| AGGTGTGTCT | ATACATAAAC | TTCAGTCATT | TTTGCTTGTG | CAGAATCATC | CCAATCTTCC | 360 |
| CAANACTGAA | TGGGCAGTCC | TGTGGCTTTC | TTCCTTTTCC | ATATTCCCAA | CAAGGCTACG | 420 |
| TGAAGTTCAA | CTCTTGATGA | GCCGCTTACA | ACAGCAGTTC | CTTAGGANCC | CAACATGACA | 480 |
| GGTGGGTCAG | ATTTCCCTAT | GAGAAACAAA | ACTGGNCACC | TACAGCAAAA | TNTCAAAATG | 540 |
| GGTAAGTCCT | TCCTTCCTCT | TCCTCCTGAT | TATNTACAAC | ATATCTCCTT | TCAAGANTAT | 600 |
| TATTTCCATC | ATGCTTATTC | CTTCCCAAAT | CTAAACCTTG | AAGGTGATTT | GAAGGGAAAC | 660 |
| CNCCATCCNN | AAAAAGAAAA | ACCCATTCCC | AAATTGAAAA | AAAACTNGGC | AGGGTATACA | 720 |
| ATACACCCCC | CANAAACTCN | CCAATTTTCC | C | | | 751 |

(2) INFORMATION FOR SEQ ID NO: 59:

(i) SEQUENCE CHARACTERISTICS:
        (A) LENGTH: 760 base pairs
        (B) TYPE: nucleic acid
        (C) STRANDEDNESS: double
        (D) TOPOLOGY: linear (xi) SEQUENCE DESCRIPTION: SEQ ID NO: 59:

CCTACATCAG TTTTATTTAA AACACAAACA AGTATTTCTC TTTCTGTAAG GGCAAATGGT        60

TCAAATAATG CGGAACACGA ACATTGACT AATACAAGTG CTTTAAATAT GAAACAAAAT        120

TATTTTTTAA AAAAGCAAAA GAATAAAGAA TATATACAAA AGGGACCTGG AATCTGTAAG        180

GTGATTCCAA AAACNAAATA AGTAGAAAAT CCATGGTGAA ACCTGAACAT TCTACCTCTG        240

CTTTGGAGAA GGGCTATCAT ACAACATTCA GTCAGCTGAA NATGGATTGG TAGAGGTGTG        300

TCTATACATA AACTTCAGTC ATTTTTGCTT GTGCANAATC ATCCCAATCT TCCCAANACT        360

GAATGGGCAG TCCTGTGGCT TTCTTCCTTT TCCATATTCC CAACAAGGCT ACGTGAAGTT        420

CAACTCTTGA TGAGCCGCTT ACAACAGCAG TTCCTTAGGA GCCAACATGA CAGGTGGGTC        480

AAATTTCCCT ATGANAAACA AAACTGGCCA CCTACAGCAA AATATCAAAA TGGGTAANTC        540

CTTCCTTCCT CTTCCTCCTG ATTATATACA ACATATCTCC TTTCAAGACT ATTATTCCAT        600

CATGCTTATT CCTTCACAAA TCTAAACCTT GAAGTGATAT GAANGAAACC NCCNTCCAGA        660

AAAGAAAACT CNANTCANAA ATGAAAAAAA CTGGCAGGTA TNCAATACAC CCCAAAACNT        720

CTCAATNTCC TGGCACANTA CAATCCATTG TTCTGCTACA                              760

(2) INFORMATION FOR SEQ ID NO: 60:

(i) SEQUENCE CHARACTERISTICS:
        (A) LENGTH: 1041 base pairs
        (B) TYPE: nucleic acid
        (C) STRANDEDNESS: double
        (D) TOPOLOGY: linear (xi) SEQUENCE DESCRIPTION: SEQ ID NO: 60:

CAAAGGCGAC AGCTGCCCAT TCCGTCACTG TGAAGCTGCA ATAGGAAATG AAACTGTTTG        60

CACATTATGG CAAGAAGGGC GCTGTTTTCG ACAGGTGTGC AGGTTTCGGC ACATGGAGAT       120

TGATAAAAAA CGCAGTGAAA TTCCTTGTTA TTGGGAAAAT CAGCCAACAG GATGTCAAAA       180

ATTAAACTGC GCTTTCCATC ACAATAGAGG ACGATATGTT GATGGCCTTT TCCTACCTCC       240

GAGCAAAACT GTGTTGCCCA CTGTGCCTGA GTCACCAGAA GAGGAAGTGA AGGCTAGCCA       300

ACTTTCAGTT CAGCAGAACA AATTGTCTGT CCAGTCCAAT CCTTCCCCTC AGCTGCGGAG       360

CGTTATGAAA GTAGAAAGTT CCGAAAATGT TCCTAGCCCC ACGCATCCAC CAGTTGTAAT       420

TAATGCTGCA GATGATGATG AAGATGATGA TGATCAGTTT TCTGAGGAAG GTGATGAAAC       480

CAAAACACCT ACCCTGCAAC CAACTCCTGA AGTTCACAAT GGATTACGAG TGACTTCTGT       540

CCGGAAACCT GCAGTCAATA TAAAGCAAGG TGAATGTTTG AATTTTGGAA TAAAAACTCT       600

TGAGGAAATT AAGTCAAAGA AAATGAAGGA AAAATCTAAG AAGCAAGGTG AGGGTTCTTC       660

AGGAGTTTCC AAGTCTTTTA CTCCACCCTG AGCCCGTTCC AAGTCCTGAA AAAGAAAATG       720

TCAGGACTGT GGTGAAGGAC AGTAACTCTC TCCAACAAAC AANGGAGAAA GAANCCTTGG       780

GTAGATTGAG TCCTACTGAN AGACGGGGGA AACGAAAANT TCAGCAAGCG GTGACAAGTG       840

ATCCTCCAAT AAAGCGTTAC CCTGCACAAA GGCTAGGGAA AAAAANTTAA ANCCCANAAA       900

ACTAACATTG ACAAAACCAC CAAAGAAAGC TCAAGNTTCC AAGTCCCCTA AGGGACCGAN       960

TAAGCATGTC AACCGGATCA ANATAATGNG GNTGCAACAG TTAAAGNTTA AAAAATTGGG      1020

GAAATTCAGT TAAAACATTT G                                                1041

(2) INFORMATION FOR SEQ ID NO: 61:

(i) SEQUENCE CHARACTERISTICS:

(A) LENGTH: 810 base pairs
        (B) TYPE: nucleic acid
        (C) STRANDEDNESS: double
        (D) TOPOLOGY: linear (xi) SEQUENCE DESCRIPTION: SEQ ID NO: 61:

CCCTACATCA GTTTTATTTA AAACACAAAC AANTATTTCT CTTTCTGTAA GGGCAAATGG      60

TTCAAATAAT GCGGAACACN AAACATTGAC TAATACAANT GCTTTAAATA TGAAACAAAA     120

TTATTTTTTA AAAAGCAAA AGAATAAANA ATATATACAA AAGGGACCTG NAATCTGTAA     180

GCTGATTCCA AAAACNAAAT AANTANAAAA TCCATGGTGA AACCTGAACA TTCTACCTCT     240

GCTTTGGANA AGGGCTATCA TACAACATTC ANTCAGCTGA AAATGGATTG GTAAAGGTGT     300

GTCTATACAT AAACTTCANT CATTTTTGCT TGTGCAAAAT CATCCCAATC TTCCCAAAAC     360

TGAATGGGCA GTCCTGTGGC TTTCTTCCTT TTCCATATTC CAACAAGGC TACNTGAANT     420

TCAACTCTTG ATNAGCCGCT TACAACAGCA GTTCCTTAGG AGCCAACATG ACAGGTGGGT     480

CAAATTTCCC TATGAANAAA CAAAACTGGC CACCTACAGC AAAATATCAA AATGGGTAAG     540

TCCTTCCTTC CTCTTCCTCC TGATTATATA CAACATATCT CCTTTCAAGA CTATTATTTC     600

CATCATGCTT ATTCCTTCAC AAATCTAAAC CTTGAGGTGA TATGAAGGAA ACCANCATCA     660

AGAAAAGAAA ACCAATTCAN AAATGAANAA AACTGGCAGG TNTACAATAC ACCCCANANC     720

ATCTCAATAT CCCTGGCACA GTTACAATTC AGTGTTCTGC TACAGCCCAT AAAATAAATA     780

TTGGCAGCTT GAATAANCNC ATTTTTTCCC                                     810

(2) INFORMATION FOR SEQ ID NO: 62:

(i) SEQUENCE CHARACTERISTICS:
        (A) LENGTH: 656 base pairs
        (B) TYPE: nucleic acid
        (C) STRANDEDNESS: double
        (D) TOPOLOGY: linear (xi) SEQUENCE DESCRIPTION: SEQ ID NO: 62:

CCCNACATCA NTTTTATTTA AAACACAAAC AATTATTTCT CTTNCTGTAA GGGCAAATGG      60

TTCAAATAAT GCGNAACACA AAACNTTGAC TAATACAATT GCTTTAAATA TNAAACAAAA     120

TTATTTTTTA AAAANCAAA AAAATAAAAA ATATNTACAA AAGGGACCTG AAATCTGTAA     180

NCTNATNCCA AAAACAAAAT AATTAAAAAA TCCATGGTNA AACCTNAACN TNCTACCTCT     240

GCTTNGGAAA AGGGCTATCA TACAACNTNC ANTCANCTNA AAATGGATNG GTAAAGGTNT     300

NTCTATACAT AAACTTCANT CATTTTNGCT TGTGCAAAAT CANCCCAATC TNCCCAAAAC     360

TNAATGGGCA NTCCTGTGGC TTNCTNCCTT TNCCATATNC CAACAAGGC TACTTNAATT     420

TCAACTCTTN ATAANCCGCT TACAACAGCA NTNCCTTAGN ANCCAACATN ACAGGTGGGT     480

CAAATTCCCC TATAAAAAAC AAAACTGGCC NCCTACANCA AAATATCAAA ATGGGTAATT     540

CCTTCCTNCC TCTNCCNCCT NATTATATAC AACATTTCTC CTTTCAAAAC TATTATTNCC     600

ATCATGCTTN TTCCTNCACA AATCTAAACC TTGANGTGAT TTGAAGGAAC CACCTC         656

(2) INFORMATION FOR SEQ ID NO: 63:

(i) SEQUENCE CHARACTERISTICS:
        (A) LENGTH: 645 base pairs
        (B) TYPE: nucleic acid
        (C) STRANDEDNESS: double
        (D) TOPOLOGY: linear (xi) SEQUENCE DESCRIPTION: SEQ ID NO: 63:

```
GAACTTCCCN ACNNCATTTT TATTTAAAAC NCAAACAATT NTTNCNCTTN CTNTANGGGC      60

AANTGGTNCA AATANTGCGN AACNCAAAAC TTTNACTAAT ACAATTGCTT TAAATNTAAA     120

NCAAANTTAT TTTTTAAAAA ACCAAAAAAA TAAAAAATNT TTCCAAANGG GACCTGAAAN     180

CTNTAACCTA ATCCCAAAAA CAAAATAATT AAAAANNCCN NGGTNAANCC TNAACNTNCT     240

NCCNCTNCTT TGNAAAAGGG CTATCANACA ACNTNCATTC NCCTAAAAAT GNATNGGTAA     300

AGGTTTTTCT ANACATAAAC TTCATTCATT TTGGCTTNTN CAAAANCACC CCAANCTNCC     360

CAAAACTNAA TGGGCNNCCT NTGGCTTNCT CCCTTTCCCA TNTNCCCAAC AAGGCTACTT     420

NAATTNCAAC NCTTNATAAC CCCCTTACAA CACCATTNCC TTAGNACCAA CATAACAGGT     480

GGGTCAAATT NCCCNATAAA AAACAAANCT GGCCCCTNCC CCAAAATNCC CAAATGGGTA     540

TTCCTNCCTN CCCTCCCCCC NGNATATATA CAACATNTCC CCTTTCANAA ATATATTCCC     600

CCACGCTTAT TCCNCCCAAA NNTAANCCTT GAAGTTATTT AAGGA                    645

(2) INFORMATION FOR SEQ ID NO: 64:

(i) SEQUENCE CHARACTERISTICS:
        (A) LENGTH: 780 base pairs
        (B) TYPE: nucleic acid
        (C) STRANDEDNESS: double
        (D) TOPOLOGY: linear (xi) SEQUENCE DESCRIPTION: SEQ ID NO: 64:

CCTTGACCTC CCAAAGTGCT GAGATTACAG GCCTGAGCCA CTGCACCTTG CCTTCCTTAC      60

CTCTTTTCTC CGACATTTTT ATGTTTCTAA CATTGAACTC TAAGGAAGCT GGTGAACAAA     120

CACGCCATAT GTATGCAGAA CACTTAACAG AATTATGCTA TGTTGTCTGT TTTTGTTTGT     180

ATTTCTTGTC CTTGCTGAAG ATTGACTTGA AATCTTAAAC TAAGTTCTCC CTCTTTATAG     240

GCGGTGACAG TGATCCTCCA TTAAAGCGTA GCCTGGCACA GAGGCTAGGG AAGAAAGTTG     300

AAGCTCCAGA AACTAACATT GACAAAACAC CAAAGAAAGC TCAAGTTTCC AAGTCTCTTA     360

AGGAGCGATT AGGCATGTCA GCTGATCCAG ATAATGAGGA TGCAACAGAT AAAGTTAATA     420

AAGTTGGTGA GATCCATGTG AAGACATTAG AAGAAATTCT TCTTGAAAGA GCCAGTCAGA     480

AACGTGGAGA ATTGCAAACT AAACTCAAGA CAGAAGGACC TTCAAAAACT GATGATTCTA     540

CTTCAGGAGC AAGAAGCTCC TCCACTATCC GTATCAAAAC CTTCTCTGAG GTCCTGGCTG     600

AAAAAAAACA TCNGCAGCAG GGAACTGAAG AGACAAAAAA GCCNAAAGGA TACAACTTGC     660

ATCAAGCTAA AGATTGATAG TGAAATTAAA AAAAACAGTA ATTTTNGCCA CCCATTGTTG     720

CCNGCAGAAG ACAATCANAA GAACCTGCAG GTAAAACAAA NTCTATGCAG GGAGGTGCCC     780

(2) INFORMATION FOR SEQ ID NO: 65:

(i) SEQUENCE CHARACTERISTICS:
        (A) LENGTH: 518 base pairs
        (B) TYPE: nucleic acid
        (C) STRANDEDNESS: double
        (D) TOPOLOGY: linear (xi) SEQUENCE DESCRIPTION: SEQ ID NO: 65:

GNACTTNCCT ACATCATTTT TATTTAAAAC ACAAACAATT NTTTCNCTTT CTGTANGGGC      60

AAATGGTTCA AATAATGCGG AACACAAAAC NTTNACTAAT ACAATTGCTT TAAATNTNAA     120

ACAAAATTAT TTTTTAAAAA ANCAAAAAAA TAAAAAATNT TTNCAAANGG GACCTGAAAT     180

CTNTAANCTN ATNCCAAAAA CAAAATAATT NAAAAATCCA NGGTGAAACC TNAACNTNCT     240

NCCNCTGCTT TGGAAAAGGG CTNTCATACA ACNTTCATTC NCCTAAAAAT GGATTGGTAA     300
```

```
ANGTTTTTNT ATACATAAAC TNCATTCATT TTTGCTTNTG CAAAATCANC CCAANCTNCC      360

CAAAACTNAA TGGGCANTCC TNTGGCTTTC TNCCTTTCCC ANATNCCCAA CAAGGCTACT      420

TNAATTTCAA CNCTTNATAA NCCGCTTACA ACANCATTTC CTTAGGANCC AACATNACGG      480

TGGGTCAAAT CCCCTATAAA AAACAAAACT GGCCNCCT                              518

(2) INFORMATION FOR SEQ ID NO: 66:

(i) SEQUENCE CHARACTERISTICS:
        (A) LENGTH: 490 base pairs
        (B) TYPE: nucleic acid
        (C) STRANDEDNESS: double
        (D) TOPOLOGY: linear (xi) SEQUENCE DESCRIPTION: SEQ ID NO: 66:

GTTAATAAAG TTGGTGAGAT CCATGTGAAG ACATTAGAAG AAATTCTTCT TGAAAGAGCC       60

AGTCAGAAAC GTGGAGAATT GCAAACTAAA CTCAAGACAG AAGGACCTTC AAAAACTGAT      120

GATTCTACTT CAGGAGCAAG AAGCTCCTCC ACTATCCGTA TCAAAACCTT CTCTGAGGTC      180

CTGGCTGAAA AAAACATCG GCAGCAGGAA GCAGAGAGAC AAAAAAGCAA AAAGGATACA       240

ACTTGCATCA AGCTAAAGAT TGATAGTGAA ATTAAAAAAA CAGTAGTTTT GCCACCCATT      300

GTTGCCAGCA GAGGACAATC AGAGGAGCCT GCAGGTAAAA CAAAGTCTAT GCAGGGAGGT      360

GCACATCAAG ACGCTGGAAG AAATTAAAACT GGAGAAGGCA CTGAGGGTGC AGCAGAGCTC    420

TGAGAGCAGC ACCAGCTCCC CGTCTCAACA CNAGGCCACT CCAAGGGCAA GGCGGCTGCT    480

GCNAATCCCC                                                            490

(2) INFORMATION FOR SEQ ID NO: 67:

(i) SEQUENCE CHARACTERISTICS:
        (A) LENGTH: 359 base pairs
        (B) TYPE: nucleic acid
        (C) STRANDEDNESS: double
        (D) TOPOLOGY: linear (xi) SEQUENCE DESCRIPTION: SEQ ID NO: 67:

CCCANCTCCN TTTTANTTNA AANCCCAACC AATTNTTCCC CTTCCGNTAN GGGCAATNGN       60

TCCAATTATN NCGAACNCCA AACCTTNAAN NATNCCAATT NCTTAAATNT TAAACCAAAT      120

TNNTTTTTTA AAAAGCCAAA NAATTAAGAA TTTTTTCCAA AGGGAACNNG AATCCNTTAG      180

GGTAATCCCA AAACCAAATT AGTTAAAAAT CCCTGGNTAA ACCCNAACNT TCCNCCNCCN     240

CCTTGGAAAA AGGGNNNCCN NCNACCTTCC ATNCNCNTAA AAATGAATGG NTAAAGNTTT     300

TTCNNNCCTT AACNTCCATC CTTTTTGNCT NTTCCAAANC CTCCCCANCC TCCCCAAAA      359

(2) INFORMATION FOR SEQ ID NO: 68:

(i) SEQUENCE CHARACTERISTICS:
        (A) LENGTH: 611 base pairs
        (B) TYPE: nucleic acid
        (C) STRANDEDNESS: double
        (D) TOPOLOGY: linear (xi) SEQUENCE DESCRIPTION: SEQ ID NO: 68:

TGAAAAAAAA CATCGGCAGC AGGAANCAGA AAGACNAAAA AGCAAAAAGG ATACTACTTG       60

CATCANGCTA ANGATTGATA GTGAAATTAA AAAAACAGTA TTTTTGCCAC CCATTGTTGC     120

CANCAGAGGA CAATCANAGG AGCCTGCAGG TAAAANNAAG TCTATGCAGG AGGTGCACAT     180

CAAGACGCTG GAAGAAATTA AACTGGAGAA GGCACTGAGG GTGCAGCANA GCTCTGAGAG     240
```

```
CAGCACCAGC TCCCCGTCTC AACACNAAGC CACTCCATGG GCNANGCGGC TGCTGCGANT      300

CNCCNAAAGA NCAGGGATGA ANGAAGAGAA GAACCTTCAG GAAGGAAATG AATTTGATTC      360

TCAGANCATT ATTATAACTG AAGCTNNANA NGCTTCNGGT GAGACCACNG GANTTGACAT      420

CACTAAAATT CCAGTCAAGA GATGTGAGAC CATGAGAGAG AAGCACATGC ACAAAACANC      480

NNGAGAGGGA AAAATCAGTC TTGACACCTC TTCGGGGAGA TGTAGCATCT TGCGGNACCC      540

AANTGGCAGA GAAACCAGTG CTCACTGCTG TGCCAGGAAT CACNCGGCAC CTGACCAAGC      600

GGCTTCCCAC A                                                          611
```

(2) INFORMATION FOR SEQ ID NO: 69:

(i) SEQUENCE CHARACTERISTICS:
        (A) LENGTH: 634 base pairs
        (B) TYPE: nucleic acid
        (C) STRANDEDNESS: double
        (D) TOPOLOGY: linear (xi) SEQUENCE DESCRIPTION: SEQ ID NO: 69:

```
CCNACATCAG TTTTATTTAA AACACAAACA AGTNTTTCNC TTTCTGTNAG GGCAAATGGT       60

TCAAATAATG CGGAACACNA AACATTGACT AATACAANTN CTTTAAATAT GAAACAAAAT      120

TATTTTTTAA AAAANCNAAA NAATAAAGAA TATNTNCAAA AGGGACCTGG AATCTGTNAG      180

CTGATTCCAA AAACNAAATA ANTTNAAAAT CCNTGGTGAA ACCTGAACAT TCTACCTCTG      240

CTTTGGAAAA GGGNTATCAT ACAACATTCA GTCNGCTGAA AATGGATTGG TAAAAGTNTN      300

TCTATACATA AACTTCAGTC ATTTTTGCTT GTNCAAAATC ATCCCAATCT TCCCAAAANT      360

GAATGGGCAG TCCTGTGGCT TTCTTCCTTT TCCATATTCC CAACAAGGNT ACNTNAANTT      420

CAACTCTTGA NNANCCGCTT ACAACAGCAG TTCCTTAGGA NCCCCATGAC AGGTGGGTCN      480

AATTTCCCTA TNAAAAACAA AACTGGGCCC TACAGCAAAA TATCCAAATG GGTNAGTCCT      540

TCCTTCCTCT TCCCCTGANT ATATACACAT ATCTCCTTTC AANAATANTA TTTCCCCATG      600

CTTATTCCTT CCCNAATCTA AACCTTGAAG TGAT                                 634
```

(2) INFORMATION FOR SEQ ID NO: 70:

(i) SEQUENCE CHARACTERISTICS:
        (A) LENGTH: 958 base pairs
        (B) TYPE: nucleic acid
        (C) STRANDEDNESS: double
        (D) TOPOLOGY: linear (xi) SEQUENCE DESCRIPTION: SEQ ID NO: 70:

```
GAAAGAAAAG CATCATGTAA AAATGAAAGC CAAGAGATGT GCCACTCCTG TAATCATCGA       60

TGAAATTCTA CCCTCTAAGA AAATGAAAGT TTCTAACAAC AAAAAGAAGC CAGAGGAAGA      120

AGGCAGTGCT CATCAAGATA CTGCTGAAAA GAATGCATCT TCCCCAGAGA AAGCCAAGGG      180

TAGACATACT GTGCCTTGTA TGCCACCTGC AAAGCAGAAG TTTCTAAAAA GTACTGAGGA      240

GCAAGAGCTG GAGAAGAGTA TGAAAATGCA GCAAGAGGTG GTGGAGATGC GGAAAAAGAA      300

TGAAGAATTC AAGAAACTTG CTCTGGCTGG AATAGGGCAA CCTGTGAAGA AATCAGTGAG      360

CCAGGTCACC AAATCAGTTG ACTTCCACTT CCGCACAGAT GAGCGAATCA ACAACATCC       420

TAAGAACCAG GAGGAATATA AGGAAGTGAA CTTTACATCT GAACTACGAA AGCATCCTTC      480

ATCTCCTGCC CGAGTGACTA AGGGATGTAC CATTGTTAAG CCTTTCAACC TGTCCCAAGG      540

AAAGAAAAGA ACATTTGATG AAACAGTTTC TACATATGTG CCCCTTGCAC AGCAAGTTGA      600
```

```
AGACTTCCAT AAACGAACCC CTAACAGATA TCATTTGAGG AGCAAGAAGG ATGATATTAA      660

CCTGTTACCC TCCAAATCTT CTGTGACCAA GATTTGCAGA GACCCACAGG ACTCCTGTAC      720

TGCAAACAAN ACACCGTGCA CGGGCTGTGA CCTGCAAAAA GTACAGCAGA GCTGGAGGCT      780

GAGGAGCTNC GAGAAATTGC AACCANTACA ANTTCCAAAG CACGTNGAAC CTTGATTCCC      840

AGAATAACTT GANGGGTGGG CCCAACCTTG CCCAAGAAAA CCACCNGTGA AANCAANCCA      900

ACGGAGCCCT ANTNGGCTTT GATTTGGGAA TTTGGGAAAN GAATNCAAGG GAGGNGAG       958

(2) INFORMATION FOR SEQ ID NO: 71:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (xi) SEQUENCE DESCRIPTION: SEQ ID NO: 71:

GGGAGGGAAA GACAAAACGT ATTTATTCCA GGCCAGGTCT TAAAATGCAC ACTGCACGGT       60

TCCCTGTTGT TATCAGCACC AGTAAGGAAA GAACGTGCCT TAACGGCAGC CCCACCCAGA      120

GCCTGCTGCG TGGCTGCTGT GAGGCTCCCC ATGAATCCAC GCAGTCTTCT TCCTCACTGG      180

TGCAGTTGGT GAGGTTTTCT ACCCTCACAG CAAAGGGATC CTTAACTATA AATTCACGGT      240

ATGCAGAGAA GAGGACAGAA TCTGATTTAC TGATTGTTCC TCATTTAAAC CATGACTTAA      300

TCTCTATCTT AGGATTTAAC TATCTTTATT TTCTGGTTAA AATTTTTAAA AAAGTGGGG       360

AGAGGGTGAG AGTCGTAAGG GGCAATAGCA ATAGAGATTA CACTGTGCTG ACACAGAGAC      420

TAAATTCTAG TCAGAGTGAA GACCATATAA AAGGCCGGCT GATGGTTTAA AGGAAGTAAC      480

TACATGGAGT CTAATCGAGA CATTCATGAN TTACATCTCA TTATTAGCCT TAGTAATGTA      540

AGAAAACAAT TCTCAACAAA ACTGGGAGTC CACAGTTGTC AAGTATGCTT TCTCANGCAC      600

GGGTAGGTAA AAGTCTGGAN AAATGGGTTC TCTCCATGCC CAATGACAAA GCAAGACGGT      660

CCTAGGTTTG AAGTTAAAAA CAGGTCCCAA TTGCCCGGGC GGTATCCGCC AGCTCACAGC      720

TGAATTTAAN CATGGAAATC CAATGGAAAA ATTGGGANAT ACNGGCACAT TCANAAGGCT      780

GGTCCTTTGA CTTATCTCCA NAACCCGGGT ACTGGC                               816

(2) INFORMATION FOR SEQ ID NO: 72:

(i) SEQUENCE CHARACTERISTICS:
        (A) LENGTH: 726 base pairs
        (B) TYPE: nucleic acid
        (C) STRANDEDNESS: double
        (D) TOPOLOGY: linear (xi) SEQUENCE DESCRIPTION: SEQ ID NO: 72:

TGAGAAAAGT GGTACAAATA CTGGGAAAAA CCTGCTCTTC TGCGTTAAGT GGGAGACAAT       60

GTCACAAGTT AAAAGCTCTT ATTCCTATGA TGCCCCCTCG GATTTCATCA ATTTTTCATC      120

CTTGGATGAT GAAGGAGATA CTCAAAACAT AGATTCATGG TTTGAGGAGA AGGCCAATTT      180

GGAGAATAAG TTACTGGGGA AGAATGGAAC TGGAGGGCTT TTCAGGGCA AAACTCCTTT       240

GAGAAAGGCT AATCTTCAGC AAGCTATTGT CACACCTTTG AAACCAGTTG ACAACACTTA      300

CTACAAAGAG GCAGAAAAAG AAAATCTTGT GGAACAATCC ATTCCGTCAA ATGCTTGTTC      360

TTCCCTGGAA GTTGAGGCAG CCATATCAAG AAAAACTCCA GCCCAGCCTC AGAGAAGATC      420

TCTTAGGCTT TCTGCTCAGA AGGATTTGGA ACAGAAAGAA AAGCATCATG TAAAAATGAA      480

AGCCAAGAGA TGTGCCACTC CTGTAATCAT CGATGAAATT CTACCCTCTA AGAAAATGAA      540
```

```
AGTTTCTAAC ANCACAAAGA AGCCAGAGGA AGAAGGCAGT GCTCATCAAG ATACTGCTGA       600

AAAGAATGCA TCTTCCCCAA GAGAAAGCCA AGGGTAGACA TACTGTGCCT TGTATGCCAC       660

CTGCANAGCA GAAGTTTCNA AAANGTACTG ANGAGCAANG AATCTGGAGA AGAGTATGAA       720

AAATGC                                                                 726
```

(2) INFORMATION FOR SEQ ID NO: 73:

(i) SEQUENCE CHARACTERISTICS:
        (A) LENGTH: 824 base pairs
        (B) TYPE: nucleic acid
        (C) STRANDEDNESS: double
        (D) TOPOLOGY: linear (xi) SEQUENCE DESCRIPTION: SEQ ID NO: 73:

```
AGGATTTAAC TATCTTTATT TTCTGGTTAA AATTTTTAAA AAAAGTGGGG AGAGGGTGAG        60

AGTCGTAAGG GGCAATAGCA ATAGAGATTA CACTGTGCTG ACACAGAGAC TAAATTCTAG       120

TCAGAGTGAA NACCCATATA AAAGGCCGGC TGATGGTTTA AAGGAAGTAA CTACATGGAG       180

TCTAATCGAG ACATTCATGA GTTACATCTC ATTATTAGCC TTAGTAATGT AAGAAAACAA       240

TTCTCAACAA AACTGGAGTC CACAGTTGTC AAGTATGCTT TCTCAGGCAC GGGTAGGTAA       300

AAGTCTGGAN AAATGGGTTC TCTCCATGCC CAATGACAAA GCAAGACGGT CCTAGGTTTG       360

AGGTTAAGAN CAGGTCCCAT TGCCGGGCGG TATCCGCAGC TCACAGCTGA NTTTAGCAGT       420

GGAATCGAGT GGAGAATTTG GGGAGATACA GGCNCAGTCA GAGGCTGGTC ACTTGACTTT       480

ATCTCCAGAC CCTGGTACTT GCGTATTGGA TTTGCCTTAT GCACCAGTTC TCTCCGTAGC       540

CTGGCCANCT CCTCTTTTTT CTGCTCTTCC TCCTGTAGTC TGGCCTCCTC CAACTGCTGG       600

GCTTTCTGGG CTTCTACCTC AGCCATTCTC TTCTCCAGCT CCCTGCCGCT CTTTGGCTCT       660

CTCTCAGTAG CCCACTGAAA ANGTCCCTGA ACNAAAAAAA CCANAAANNG GCCCTCACAA       720

CTGATTTCNT CTCTTTCTTG GGGAACCAAG GGCCCCTGAA AAAANAAACG GTGTTTGGAA       780

CAAACCNTGA AACAAGCNGC CTCCTTCTGC CTGTCCCAAT TCCT                       824
```

(2) INFORMATION FOR SEQ ID NO: 74:

(i) SEQUENCE CHARACTERISTICS:
        (A) LENGTH: 399 base pairs
        (B) TYPE: nucleic acid
        (C) STRANDEDNESS: double
        (D) TOPOLOGY: linear (xi) SEQUENCE DESCRIPTION: SEQ ID NO: 74:

```
GGTTTGNAGG GAAAAANAAA ACTTTTTTTT CCCAGNCCAG TTCTTAAAANT NCCCCNNGCN       60

NGGTCCCCTN TNTTTTTCNC CCCCATTAAG GAAAAAACTT GCNTNANCGG NAGCCCCCCC      120

CAAAACCTNC TGCTTGGCTG CTTTAAGGNC CCCATAANNC CCCCCATNNT CCTCCCCCAC      180

TGGTNCATTG GTNAGGTTTC CTCCCCCCCN CCAAAGGNNT CCTTACNTAT AAATCCCNGG      240

TTTNCAAAAA AAAANANAAA ACCAATTTCN GATNNTCCCC CTTNAANCCA GNACTTAATC      300

CCTNTCTNAG GATTNAACAA CCTTTTTTTN CGGGTTAAAA TTTTTAAAAA AATTNGGGAA      360

ANGGTTAAAT CCTTAGGGGG AATNCCNATA AAAATTACC                             399
```

(2) INFORMATION FOR SEQ ID NO: 75:

(i) SEQUENCE CHARACTERISTICS:
        (A) LENGTH: 826 base pairs
        (B) TYPE: nucleic acid (C) STRANDEDNESS: double
        (D) TOPOLOGY: linear (xi) SEQUENCE DESCRIPTION: SEQ ID NO: 75:

| | | | | | |
|---|---|---|---|---|---|
| GTCAAATGCT | TGTTCTTCCC | TGGAAGTTGA | GGCAGCCATA | TCAAGAAAAA | CTCCAGCCCA | 60 |
| GCCTCAGAGA | AGATCTCTTA | GGCTTTCTGC | TCAGAAGGAT | TTGGAACAGA | AAGAAAAGCA | 120 |
| TCATGTAAAA | ATGAAAGCCA | AGAGATGTGC | CACTCCTGTA | ATCATCGATG | AAATTCTACC | 180 |
| CTCTAAGAAA | ATGAAAGTTT | CTAACAACAA | AAAGAAGCCA | GAGGAAGAAG | GCAGTGCTCA | 240 |
| TCAAGATACT | GCTGAAAAGA | ATGCATCTTC | CCCAGAGAAA | GCCAAGGGTA | GACATACTGT | 300 |
| GCCTTGTATG | CCACCTGCAA | AGCAGAAGTT | TCTAAAAAGT | ACTGAGGAGC | AAGAGCTGGA | 360 |
| GAAGAGTATG | AAAATGCAGC | AAGAGGTGGT | GGAGATGCGG | AAAAAGAATG | AAGAATTCAA | 420 |
| GAAACTTGCT | CTGGCTGGAA | TAGGGCAACC | TGTGAAGAAA | TCAGTGAGCC | AGGTCACCAA | 480 |
| ATCAGTTGAC | TTCCACTTCC | GCACAGATGA | GCGAATCNAA | CAACATCCTA | NGAACCAGGA | 540 |
| GGAATATAAG | GGAAGTGAAC | TTTACATCTG | AACTACGAAA | GCATCCTTCA | TCTCCTGCCC | 600 |
| GAANTGACTA | AGGGGATGTT | CCATTGTTAA | GCCTTTCAAC | CTGTCCCNGG | GAAAGAANAG | 660 |
| AACNTTTGAT | GAAACAGTTT | CTACATATGT | GCCCCTTGCC | CNGCAAGTTG | AAGACTTCCN | 720 |
| TAANCGAACC | CTNACTGATT | TCTTTTGANG | AACCAGAANG | GNTGATTTTN | CCCTGTTTCC | 780 |
| CTCCAATCTT | CTGTGAACAA | GATTTGGCCG | AANACCCCCG | AACCCC | | 826 |

(2) INFORMATION FOR SEQ ID NO: 76:

(i) SEQUENCE CHARACTERISTICS:
        (A) LENGTH: 770 base pairs
        (B) TYPE: nucleic acid
        (C) STRANDEDNESS: double
        (D) TOPOLOGY: linear (xi) SEQUENCE DESCRIPTION: SEQ ID NO: 76:

| | | | | | |
|---|---|---|---|---|---|
| GGGAAAGACA | AAACGTATTT | ATTCCAGGCC | AGGTCTTAAA | ATGCACACTG | CACGGTTCCC | 60 |
| TGTTGTTATC | AGCACCAGTA | AGGAAAGAAC | GTGCCTTAAC | GGCAGCCCCA | CCCANAGCCT | 120 |
| GCTGCGTGGC | TGCTGTGAGG | CTCCCCATGA | ATCCACGCAG | TCTTCTTCCT | CACTGGTGCA | 180 |
| GTTGGTGAGG | TTTTCTACCC | TCACAGCAAA | GGGATCCTTA | ACTATAAATT | CACGGTATGC | 240 |
| ANAGAANAGG | ACAGAATCTG | ATTTACTGAT | TGTTCCTCAT | TTAAACCATG | ACTTAATCTC | 300 |
| TATCTTAGGA | TTTAACTATC | TTTATTTTCT | GGTTAAAATT | TTTAAAAAAA | GTGGGGAGAG | 360 |
| GGTGAGAGTC | GTAAGGGGCA | ATAGCAATAG | AGATTACACT | GTGCTGACAC | AGAGACTAAA | 420 |
| TTCTAGTCAG | AGTGAAGACC | CATATAAAAG | GCCGGCTGAT | GGTTTAAAGG | AAGTAACTAC | 480 |
| ATGGAGTCTA | ATCGAGACAT | TCATGAGTTN | CATCTCATTA | TTAGCCTTAG | TAATGTAAGA | 540 |
| AAACNATTCT | CAACAAAACT | GGAGTCCACA | GTTGTCAANT | NTGCTTTCTC | AGGCACGGGT | 600 |
| AGGTNAAAAT | CTGGANAAAT | GGGTTCTCTC | CATGCCCAAT | GACAANCAAN | ANGGTCCTAG | 660 |
| GTTTGAAGTT | AAAAACANGT | CCCATTGCCG | GCGGTATCCG | CAGCTCACAG | CTGAATTTAC | 720 |
| CNGTGGAATC | AANTGGAAAA | TTTGGGAAAA | TACNGGCCCA | ATCAAAAGGT | | 770 |

(2) INFORMATION FOR SEQ ID NO: 77:

(i) SEQUENCE CHARACTERISTICS:
        (A) LENGTH: 593 base pairs
        (B) TYPE: nucleic acid
        (C) STRANDEDNESS: double
        (D) TOPOLOGY: linear (xi) SEQUENCE DESCRIPTION: SEQ ID NO: 77:

```
GAAGANCTGA GCAGCACAGC ACTGGTGAAG AAGAGCTGCC TGGCGGAGCT CCTCCGGCTT      60
TACACCAAAA GCAGCAGCTC TGATGAGGAG TACATTTATA TGAACAAAGT GACCATCAAC     120
AAGCAACAGA ATGCAGAGTC TCAAGGCAAA GCGCCTGAGG AGCAGGGCCT GCTACCCAAT     180
GGGGAGCCCA GCCAGCACTC CTCGGCCCCT CAGAAGAGCC TTCCAGACCT CCCGCCACCC     240
AAGATGATTC CAGAACGGAA ACAGCTTGCC ATCCCAAAGA CGGAGTCTCC AGAGGGCTAC     300
TATGAAGAGG CTGAGCCATA TGACACATCC CTCAATGAGG ACGAGAGGC TGTGAGCAGC      360
TCCTACGAGT CCTACGATGA ANAGGACGGC AGCAAGGGCA AGTCGGCCCC TTACCANTGG     420
NCCTCGCCGG AGGCCGGCAT CGANCTGATG CGTGACGCCC GCNTCTGCGC CTTCCTGTGG     480
CGCAAGAAAG TGGCTGGGAC AGTGGGCCAA GCAGCTCTGT GTCATCNAGG ACAACAGGCT     540
TCTGTGCTNC NAATCCTCCA AGGACCCCNG CCCTCAGCTG GACGTGAACC TAC            593
```

(2) INFORMATION FOR SEQ ID NO: 78:

(i) SEQUENCE CHARACTERISTICS:
        (A) LENGTH: 1024 base pairs
        (B) TYPE: nucleic acid
        (C) STRANDEDNESS: double
        (D) TOPOLOGY: linear (xi) SEQUENCE DESCRIPTION: SEQ ID NO: 78:

```
AAGAGATTGA AGCAAATGAA TGGAAGAAGA AATACGAAGA GACCCGGCAA GAAGTTTTGG      60
AGATGAGGAA AATTGTAGCT GAATATGAAA AGACTATTGC TCAAATGATT GAAGATGAAC     120
AAAGGACAAG TATGACCTCT CAGAAGAGCT TCCAGCAACT GACCATGGAG AAGGAACAGG     180
CCCTGGCTGA CCTTAACTCT GTGGAAAGGT CCCTTTCTGA TCTCTTCAGG AGATATGAGA     240
ACCTGAAAGG TGTTCTGGAA GGGTTCAAGA AGAATGAAGA AGCCTTGAAG AAATGTGCTC     300
AGGATTACTT AGCCAGAGTT AAACAAGAGG AGCAGCGATA CCAGGCCCTG AAAATCCACG     360
CAGAAGAGAA ACTGGACAAA GCCAATGAAG AGATTGCTCA GGTTCGAACA AAAGCAAAGG     420
CTGAGAGTGC AGCTCTCCAT GCTGGACTCC GCAAAGAGCA GATGAAGGTG GAGTCCCTGG     480
AAAGGGCCCT GCAGCAGAAG AACCAAGAAA TTGAAGGAAC TGACAAAAAT CTGTGATGAG     540
CTGATTGCAA AGCTGGGAAA GACTGACTGA GACACTCCCC CTGTTAGCTC AACAGATCTG     600
CATTTGGCTG CTTCTCTTGT GACCACAATT ATCTTGCCTT ATCCAGGAAT AATTGCCCCT     660
TTGCAGANGA AAAAATATA CTTAANAAAA GCACATGCCT ACTGCTGCCT GTCCCGCTTT      720
GCTGCCAATG CAACAGCCCT GGAAGAAAAC CCTATANGGN TGCATAGTCT AAAAAGGGAG     780
TTGTNGACTN GACAGTGCTG GGAGCCTNCT AGTTTCCCCC CNATGAAAGG TTCCCTTAGG     840
CTGCTGAGTT TGGGGTTTGT GATTTAACCT TAAGTTTGTT TTAAAGTCCA NCTTAACTTT     900
CCCAAATTGT GTTTAAAATT TGTAACNCCC CCTTTGGGGT CTTCCCAACA ACCGGTCCGA     960
TTTTTTTGGN GATCGGTTTA ACCCTTTTAA TTTTTTAGTA NCCAGTGGGG TTTAATTTAG    1020
GGGA                                                                 1024
```

(2) INFORMATION FOR SEQ ID NO: 79:

(i) SEQUENCE CHARACTERISTICS:
        (A) LENGTH: 734 base pairs
        (B) TYPE: nucleic acid
        (C) STRANDEDNESS: double
        (D) TOPOLOGY: linear (xi) SEQUENCE DESCRIPTION: SEQ ID NO: 79:

```
GAGACAAGAT CTTGCTGTCA CCCAGGATGG AGTGCAGTGG CATGATCATG GCTCACTGCA        60

GCCTTGACCT CCCAGGCTCC CACCTCAGCC TCCCAAGTAG CTGGGACCAC AGGCACGTGC       120

CACCATGCCC AGCTAATTTT TATTTTGGTA NANACAAGGT TTCACCATGT TGCCTAGGTA       180

GGTTTCAAAC TCCTGGACTC AAGTGATCCT CCTGCCTCGG CCTTCCACAG TGTTGGGATT       240

ACAGGAATAA GCCACTGTGC CCGGCCCTTT TTCTCTTCTG TAACAGANTT TATTACTGCC       300

TAGCTAGCAG GTTATTTGGC CCTCACATGT GTTGAGGCAA ACTCTATACT ATATTCTTAC       360

TCTCCANAGT TCCAAAATCC TTTATTTTTA AANAAAAATA AACAAACATA CTTCATTCTG       420

CCCAGTATAT TCTCTTGATC TGTACAAGCT ACGATTTTAA TTCTCTTTGG GAGAGGAAGC       480

ATCTGTTAAG TTCGAATGGG GGATATTTCC TCATAACGGT CATGGCTGAN AAGCCAGGAC       540

AATTATCACT TAACGAAGGT CCTTTGGTGC TCCCTGTGCA TCAGCTTCAT TCACTGGGGT       600

CAGGTTCTTA AGGGGTCTCT TCCACCAATG TGCTAGGGAA GGGCTGCCAT CACCTCTGTT       660

TAACACATAG CTACTTTCTT AAACCNATAA GCTTAAAAAA GANGACTATG GAATTACCAA       720

TGGAAGGCNT ATAA                                                        734

(2) INFORMATION FOR SEQ ID NO: 80:

(i) SEQUENCE CHARACTERISTICS:
        (A) LENGTH: 592 base pairs
        (B) TYPE: nucleic acid
        (C) STRANDEDNESS: double
        (D) TOPOLOGY: linear (xi) SEQUENCE DESCRIPTION: SEQ ID NO: 80:

GTTATGAANA CCTTTCCAAA TTCATTTGTA TTTCTGTTAA ATTTATTTTT TACTTTTAGA        60

GTGGCTATCA TTATAATGTA ATTTAAAATT ATATTTGTAA AAGTGACTAT TGGAGTGAGT       120

ACGAATTTTG TTTATANATC TATGATAAAT GCATTCTCCC TNTAGGAGGT AGAANAGTAT       180

ACAGCTGTNT ATAATAAGCT TCGCTATGAA CATACATTTC TCAAGTCAGA ATTTGAACAC       240

CAGAAGGAAG AGTATGCACG TNTTTTAGAT GAANGAAACN ATAAACTATG AATCAGAGAT       300

NGCAANACTG GAGGAAGATN AAGAAGAACT ACGTANCCAG CTGCTTAATG TNGATCTCAC       360

ANAAGACAGC AAACGAGTGG AACAACTTGC TCGAGAAAAA GTCTATTTGT GTCCAAAATT       420

AAGANGTTTA GAGGCTGAAG TACCNGAATT AAAGGCTGAA NAGGAGAATT CTGANGCTCA       480

GGTGAAAAT GCCCAAANAA TACACGTGCG GCAGTTGGCT GAGATGCACG CTACAGTCAG       540

ATCCCTGGAG GCTGACAANC AATCANCTAA TTTACGGGCA NAACGCTTGG AA              592

(2) INFORMATION FOR SEQ ID NO: 81:

(i) SEQUENCE CHARACTERISTICS:
        (A) LENGTH: 373 base pairs
        (B) TYPE: nucleic acid
        (C) STRANDEDNESS: double
        (D) TOPOLOGY: linear (xi) SEQUENCE DESCRIPTION: SEQ ID NO: 81:

AAAAAAAAAT TAAGCTCTTT AATTATGTGC ACACAGATTT TAGAAAAGGT AGCCTTTTGT        60

ATATANATAC CTTTACATTC TTTAGGNTGA NTTTTAAATT GTCATCTTTT TTCAACTACA       120

GTTTTTGTNT ATAGTAAACC ANAANATGTG TNTGGACCCT GTTATGGNCA AGCATCTCAA       180

AGATGAAGAN AGAATTAATG ATAGTTATAT TTCACTCAAA ATGCCAAAAA AAAAAATTCA       240

ACAAAGTAAA AATTTTAAAA CTTGACTCTA ACTAGTTCCT TTTTGTTTTA CATTCTCAAA       300
```

```
CCATTGTNAA ATATTCTAAA TATCTCTGAA AATTTCTCTT TTAATGCTTC ACTTGTNTAA      360

TCTTAAAATC CTG                                                         373
```

(2) INFORMATION FOR SEQ ID NO: 82:

(i) SEQUENCE CHARACTERISTICS:
        (A) LENGTH: 661 base pairs
        (B) TYPE: nucleic acid
        (C) STRANDEDNESS: double
        (D) TOPOLOGY: linear (xi) SEQUENCE DESCRIPTION: SEQ ID NO: 82:

```
CACACCTGGT GGTCCTGAAG ACAGCCCAGG ACCCAGGGAT CTCCCCCAGC CAGAGTCTGT       60

GTGCGGAAAG TTCCAGAGGC CTCAGTGCAG GCTCCCTGTC GGAGAGTGCA GTTGGGCCCG      120

TGGAGGCATG CTGCCTGGTC ATCCTGGCTG CAGAGAGCAA GGTCGCTGCG GAGGAGCTTT      180

GCTGTCTGCT AGGCCAGGTC TTCCAGGTTG TTTACACGGA GTCACCATCG ACTTTCTGG       240

ACAGAGCGAT ATTTGATGGG GCCTCTACCC CGACCCACCA CCTGTCCCTG CACAGCGATG      300

ACTCTTCTAC AAAAGTGGAC ATTAAGGAGA CCTACGAGGT GGAAGCCAGC ACTTTCTGCT      360

TCCCTGAATC TGTGGATGTG GGTGGTGCAT CACCCCACAG CAAGACCATC AGTGAGAGCG      420

AGCTGAGCGC CAGCGCCACT GAGCTGCTGC AGGACTACAT GCTGACGCTG CGCACCAAGC      480

TGTCATCACA GGAGATCCAG CAGTTTGCAG CACTGCTGCA CGAGTACCGC AATGGGGCCT      540

CTATCCACGA NTTCTGCATC AACCTGCGGC AGCTCTACGG GGACAGCCGC AAGTTCCTGC      600

TGCTTGGTCT GAAGCCCTTC ATCCCTGAAA ANGACAGCCA GCACTTCNAG AACTTCCTGG      660

A                                                                     661
```

(2) INFORMATION FOR SEQ ID NO: 83:

(i) SEQUENCE CHARACTERISTICS:
        (A) LENGTH: 401 base pairs
        (B) TYPE: nucleic acid
        (C) STRANDEDNESS: double
        (D) TOPOLOGY: linear (xi) SEQUENCE DESCRIPTION: SEQ ID NO: 83:

```
AAATTATTCA CATTGCAGTA AACTTCTTTT TAAGGTCTCT GAAAGTTACA ATAGGAACAT       60

CATGTGCAAA ACTGACAGCC GTCCAAGGGC CCAGCCGACA GGACTGGCTC TCCCTGCCCG      120

CTCGGCCGGG CCCTCCCCGA GCGGGGACAC ACTGCAGGGC TTGGCTGAAC CCTGGTGGAC      180

AAGGCAAANA NCCTTCCACC CCGCACTGAG GCTCGTGTCC CTCGGCAGCT CCCTGCTCCT      240

TCACAGTAAA NGACCTGGGC CGCCCGGGGC CATCTGCACC GGGCGCCTCT CCCTGGCCAC      300

CACCAAGGGC TGACACGCAG GTCTGGGCAG CTCCTTCTGG GAAGGCCTAT GACGACTGCG      360

CCGAAGGTGT GGGTGCCCCC CCATCCACTG TCCATCATGC C                         401
```

(2) INFORMATION FOR SEQ ID NO: 84:

(i) SEQUENCE CHARACTERISTICS:
        (A) LENGTH: 1347 base pairs
        (B) TYPE: nucleic acid
        (C) STRANDEDNESS: double
        (D) TOPOLOGY: linear (xi) SEQUENCE DESCRIPTION: SEQ ID NO: 84:

```
AAGATCAGCG ATATCACGCG TCCCCCGGAG CATCGCGTGC AGGAGCCATG GCGCGGGAGC       60

TATACCACGA AGAGTTCGCC CGGGCGGGCA AGCAGGCGGG GCTGCAGGTC TGGAGGATTG      120
```

| | |
|---|---|
| AGAAGCTGGA GCTGGTGCCC GTGCCCCAGA GCGCTCACGG CGACTTCTAC GTCGGGGATG | 180 |
| CCTACCTGGT GCTGCACACG GCCAAGACGA GCCGAGGCTT CACCTACCAC CTGCACTTCT | 240 |
| GGCTCGGAAA GGAGTGTTCC CAGGATGAAA GCACAGCTGC TGCCATCTTC ACTGTTCAGA | 300 |
| TGGATGACTA TTTGGGTGGC AAGCCAGTGC AGAATAGAGA ACTTCAAGGA TATGAGTCTA | 360 |
| ATGACTTTGT TAGCTATTTC AAAGGCGGTC TGAAATACAA GGCTGGAGGC GTGGCATCTG | 420 |
| GATTAAATCA TGTTCTTACG AACGACCTGA CAGCCAAGAN GCTCCTACAT GTGAAGGGTC | 480 |
| GTANAGTGGT GAGAGCCACA GAATTCCCCT TAGCTGGGAC AGTTTCAACA AGGGTGACTG | 540 |
| CTTCATCATT GACCTTGGCA CCGAAATTTA TCANTTGGTG TGGTTCCTCN TGCAACAAAT | 600 |
| ATGAACGTCT GAAGGCAAAC CAGGTAGCTA CTGGCATTCG GTACAATGAA AGGAAAGGAA | 660 |
| GGTCTGAACT AATTGTCGTG GAANAAGGAA GTGAACCCTC AGAACTTATA AAGGTCTTAG | 720 |
| GGGAAAAGCC AGAGCTTCCA GATGGAGGTG ATGATGATGA CATTATANCA GACATAAGTA | 780 |
| ACAGGAAAAT GGCTAAACTA TACATGGTTT CAGATGCAAG TGGCTCCATG AGAGTGACTG | 840 |
| TGGTGGCANA AGAAAACCCC TTCTCANTGG CAATGCTGCT GTCTGAAGAA TGCTTTATTT | 900 |
| TGGACCACGG GGCTGCCAAA CAAATTTTCG TATGGAAAGG TAAAGATGCT AATCCCCAAG | 960 |
| AGAGGAAGGC TGCAATGAAG ACAGCTGAAG AATTTCTACA GCAAATGAAT TATTCCAAGA | 1020 |
| ATACCCAAAT TCAAGTTCTT CCAGAAGGAG GTGAAACACC AATCTTCAAA CAGTTTTTTA | 1080 |
| AGGACTGGAG AGATNAACGA TCAGAGTGAT GGCTTCGGGA AAGTTTATGT CACAGAGAAA | 1140 |
| GTGGCTCAAN TNNAACNAAT TCCCTTTGAT GCCTCNNAAT TACNCAGTTC TCCGCAGATG | 1200 |
| GCAGCCCAGC ACAATATGGT GGATGATGGT TCTGGCCAAG TGGAAATTTG GCGTGTNCAA | 1260 |
| AACAATGGTA GGATCCAAGT TGACCNNAAC TCCTATGGTG ACTCCCATGG TGGTGACTGC | 1320 |
| TACTTCATAC TCTACACCTA TCCCTGA | 1347 |

(2) INFORMATION FOR SEQ ID NO: 85:

(i) SEQUENCE CHARACTERISTICS:
        (A) LENGTH: 3441 base pairs
        (B) TYPE: nucleic acid
        (C) STRANDEDNESS: double
        (D) TOPOLOGY: linear (xi) SEQUENCE DESCRIPTION: SEQ ID NO: 85:

| | |
|---|---|
| ATGTTTCTAA CATTGAACTC TAAGGAAGCT GGTGAACAAA CACGCCATAT GTATGCAGAA | 60 |
| CACTTAACAG AATTATGCTA TGTTGTCTGT TTTTGTTTGT ATTTCTTGTC CTTGCTGAAG | 120 |
| ATTGACTTGA AATCTTAAAC TAAGTTCTCC CTCTTTATAG GCGGTGACAG TGATCCTCCA | 180 |
| TTAAAGCGTA GCCTGGCACA GAGGCTAGGG AAGAAAGTTG AAGCTCCAGA AACTAACATT | 240 |
| GACAAAACAC CAAGAAAAGC TCAAGTTTCC AAGTCTCTTA AGGGAGCGAT TAGGCATGTC | 300 |
| AGCTGATCCA GATAATGAGG ATGCAACAGA TAAAGTTAAT AAAGTTGGTG AGATCCATGT | 360 |
| GAAGACATTA AAGAAATTC TTCTTGAAAG AGCCAGTCAG AAACGTGGAG AATTGCAAAC | 420 |
| TAAACTCAAG ACAGAAGGAC CTTCAAAAAC TGATGATTCT ACTTCAGGAG CAAGAAGCTC | 480 |
| CTCCACTATC CGTATCAAAA CCTTCTCTGA GGTCCTGGCT GAAAAAAAAC ATCGGCAGCA | 540 |
| GGAAGCAGAG AGACAAAAAA GCAAAAAGGA TACAACTTGC ATCAAGCTAA AGATTGATAG | 600 |
| TGAAATTAAA AAAACAGTAG TTTTGCCACC CATTGTTGCC AGCAGAGGAC AATCAGAGGA | 660 |
| GCCTGCAGGT AAAACAAAGT CTATGCAGGG AGGTGCACAT CAAGACGCTG GAAGAAATTA | 720 |
| AACTGGAGAA GGCACTGAGG GTGCAGCAGA GCTCTGAGAG CAGCACCAGC TCCCCGTCTC | 780 |

-continued

| | |
|---|---|
| AACACGAGGC CACTCCAAGG GCAAGGCGGC TGCTGCGAAT CCCCAAAAGA ACAGGGATGA | 840 |
| AAGAAGAGAA GAACCTTCAG GAAGGAAATG AATTTGATTC TCAGAGCATT ATTATAACTG | 900 |
| AAGCTAAAGA AGCTTCAGGT GAGACCACAG GAGTTGACAT CACTAAAATT CCAGTCAAGA | 960 |
| GATGTGAGAC CATGAGAGAG AAGCACATGC ACAAAACAAC AGGAGAGGGA AAAATCAGTC | 1020 |
| TTGACACCTC TTCGGGGAGA TGTAGCCTCT TGCAATACCC AAGTGGCAGA GAAACCAGTG | 1080 |
| CTCACTGCTG TGCCAGGAAT CACACGGCAC CTGACCAAGC GGCTTCCCAC AAAGTCATCC | 1140 |
| CAGAAGGTGG AGGTAGAAAC CTCAGGGATT GGAGACTCAT TATTGAATGT GAAATGTGCA | 1200 |
| GCACAGACCT TGGAAAAAAG GGGTAAAGCT AAACCCAAAG TGAACGTGAA GCCATCTGTG | 1260 |
| GTTAAAGTTG TGTCATCCCC CAAATTGGCC CCAAAACGTA AGGCAGTGGA GATGCACGCT | 1320 |
| GCTGTCATTG CCGCTGTGAA CCACTCAGCT CCAGCAGTGT CCTACAGGAA CCCCCAGCCA | 1380 |
| AAAAGGCAGC TGTGGCTGTT GTCCCGCTTG TCTCTGAGGA CAAATCAGTC ACTGTGCCTG | 1440 |
| AAGCAGAAAA TCCTAGAGAC AGTCTTGTGC TGCCTCCAAC CCAGTCCTCT TCAGATTCCT | 1500 |
| CACCCCCGGA GGTGTCTGGC CCTTCCTCAT CCCAAATGAG CATGAAAACT CGCCGACTCA | 1560 |
| GCTCTGCCTC AACAGGAAAG CCCCCACTCT CTGTGGAGGA TGATTTTGAG AAACTAATAT | 1620 |
| GGGAGATTTC AGGAGGCAAA TTGGAAGCTG AGATTGACCT GGATCCTGGG AAAGATGAAG | 1680 |
| ATGACCTTCT GCTTGAGCTA TCAGAAATGA TTGATAGCTG AAGGGTGGTA GTGAGGACAC | 1740 |
| TTTAAAAAAA AATCGCCAAA AAACTGGACT TAGTTTCATC TATTGTAACA TTTACCTGAG | 1800 |
| ATGATCATTT CTTTAGTCTA GAATTTGCCC CAAATCAGAA GTATACCTCT GAATTATCTG | 1860 |
| TATGTGTCCT GGATTCCTTG GGGTCAGATT TTTAAAGTTA CTTTATAACC ATTTTGTCCA | 1920 |
| TTTGATGCCA TTGTTTATCA TCTTTTGAGA AAAAAGTTCT GTCATACCCT TCTCTCCACA | 1980 |
| AAAAAGAGAC TGAGAGGGAG ATCAAGTGAA AGGGTGCAAG CGAACTTAGT GACTCCTTGA | 2040 |
| GGTGTTTGTC AGTTTTGGCT TTTTTCTTCT TTGTTGTATT CTTTATGTAT TGTCTTGATG | 2100 |
| TACTTAATAT TACCTGAGTT TGAAATGGAT GAAGACAGCT GCTACCATTA AGGACCAAAT | 2160 |
| TTTATGCTAC CACTAAACAA AAATACCCAC TCAGTCTGTG TTAAATTGTA TGTCTTTTTA | 2220 |
| AAGGTATTTA AAGATTCAAC TAAGCTTTAA AGAGGGCTGA GCAGCTCAGG AAGCCTGTAA | 2280 |
| TGTGGGCATA ACTCTTTGGA CCTGATCTTG ATGCTTCTGC TGCTCTGTTA GCCTCTGAAG | 2340 |
| AGCAATATCT AATTTATTAT TACTGTAATT TTTTAAAAGG CTTTAAAGTG CCTCAGGGGT | 2400 |
| CCCCTGAAAC TAATTTTCTA TTTCTGGGAT TCCCTGGATT CATTATATGA GATGGTGACA | 2460 |
| TGATTAGAGG AATTCTTTTT TAGTATGAAA ATTGTCCCTT TCTTCTTCA GTACTTGCCT | 2520 |
| CCTTGCTGGC ATTGAATTAA CACAGGGACA AAATTTGGTT AATTTTTTAT TTCTAACTCT | 2580 |
| CCCAACAAAC CCCTGTTGCC CAGTATTTGT TTGGTGGCCT TTAACCACCT GAGGGAAAAA | 2640 |
| ATGAGCTTAT TCAAGCTGCC AATATTTATC TATGGGCTGT AGCAGTACAC TGAATTGTAC | 2700 |
| TGTGCCAGGG ATATTGAGAT GCTCTGGGGG TGTATTGTAT ACCTGCCAGT TTTCTTCATT | 2760 |
| TCTGAATTGA GTTTTCTTTT CTTGATGTTG GTTTCCTTCA TATCACCTCA AGGTTTAGAT | 2820 |
| TTGTGAAGGA ATAAGCATGA TGGAAATAAT AGTCTTGAAA GGAGATATGT TGTATATAAT | 2880 |
| CAGGAGGAAG AGGAAGGAAG GACTTACCCA TTTTGATATT TTGCTGTAGG TGGCCAGTTT | 2940 |
| TGTTTCTCAT AGGGAAATNT GACCCACCTG TCATGTTGGC TCCCTAAGGA ACTGCTGTTG | 3000 |
| TAAGCGGCTC ATCAAGAGTT GAACTTCACG TAGCCTTGTT GGGAATATGG AAAAGGAAGA | 3060 |
| AAGCCACAGG ACTGCCCATT CAGTTTTGGG AAGATTGGGA TGATTTTGCA CAAGCAAAAA | 3120 |
| TGACTGAAGT TTATGTATAG ACACACCTTT ACCAATCCAT NTTCAGCTGA CTGAATGTTG | 3180 |

| TATGATAGCC CTTCTCCAAA GCAGAGGTAG AATGTTCAGG TTTCACCATG GATTTTCTAC | 3240 |

| TTATTTCGTT TTTGGAATCA CCTTACAGAT TCCAGGTCCC TTTTGTATAT ATTCTTTATT | 3300 |

| CTTTTGCTTT TTTAAAAAAT AATTTTGTTT CATATTTAAA GCACTTGTAT TAGTCAATGT | 3360 |

| TTCGTGTTCC GCATTATTTG AACCATTTGC CCTTACAGAA AGAGAAATAC TTGTTTGTGT | 3420 |

| TTTAAATAAA ACTGATGTAG G | 3441 |

(2) INFORMATION FOR SEQ ID NO: 86:

(i) SEQUENCE CHARACTERISTICS:
        (A) LENGTH: 1016 base pairs
        (B) TYPE: nucleic acid
        (C) STRANDEDNESS: double
        (D) TOPOLOGY: linear (xi) SEQUENCE DESCRIPTION: SEQ ID NO: 86:

| GTCAAATGCT TGTTCTTCCC TGGAAGTTGA GGCAGCCATA TCAAGAAAAA CTCCAGCCCA | 60 |

| GCCTCAGAGA AGATCTCTTA GGCTTTCTGC TCAGAAGGAT TTGGAACAGA AAGAAAAGCA | 120 |

| TCATGTAAAA ATGAAAGCCA AGAGATGTGC CACTCCTGTA ATCATCGATG AAATTCTACC | 180 |

| CTCTAAGAAA ATGAAAGTTT CTAACAACAA AAAGAAGCCA GAGGAAGAAG GCAGTGCTCA | 240 |

| TCAAGATACT GCTGAAAAGA ATGCATCTTC CCCAGAGAAA GCCAAGGGTA GACATACTGT | 300 |

| GCCTTGTATG CCACCTGCAA AGCAGAAGTT TCTAAAAAGT ACTGAGGAGC AAGAGCTGGA | 360 |

| GAAGAGTATG AAAATGCAGC AAGAGGTGGT GGAGATGCGG AAAAAGAATG AAGAATTCAA | 420 |

| GAAACTTGCT CTGGCTGGAA TAGGGCAACC TGTGAAGAAA TCAGTGAGCC AGGTCACCAA | 480 |

| ATCAGTTGAC TTCCACTTCC GCACAGATGA GCGAATCAAA CAACATCCTA AGAACCAGGA | 540 |

| GGAATATAAG GAAGTGAACT TTACATCTGA ACTACGAAAG CATCCTTCAT CTCCTGCCCG | 600 |

| AGTGACTAAG GGATGTACCA TTGTTAAGCC TTTCAACCTG TCCCAAGGAA AGAAAAGAAC | 660 |

| ATTTGATGAA ACAGTTTCTA CATATGTGCC NCCTTGCACA GCAAGTTGAA GACTTCCATA | 720 |

| AACGAACCCC TAACAGATAT CATTTGAGGA GCAAGAAGGA TGATATTAAC CTGTTACCCT | 780 |

| CCAAATCTTC TGTGACCAAG ATTTGCAGAG ACCCACAGAC TCCTGTACTG CAAACCAAAC | 840 |

| ACCGTGCACG GGCTGTGACC TGCAAAAGTT ACAGCAGAGC TGGAGGCTGA GGAGCTCGAG | 900 |

| AAATTGCAAC AATACAAATT CAAAGCACGT GAACTTGATC CCAGAATACT TGAAGGTGGG | 960 |

| CCCATCTTGC CAAGAAACC ACCTGTGAAA CCACGCCGAG CCCTATGCCT CGTGCC | 1016 |

(2) INFORMATION FOR SEQ ID NO: 87:

(i) SEQUENCE CHARACTERISTICS:
        (A) LENGTH: 1135 base pairs
        (B) TYPE: nucleic acid
        (C) STRANDEDNESS: double
        (D) TOPOLOGY: linear (xi) SEQUENCE DESCRIPTION: SEQ ID NO: 87:

| AGGAATTGGG ACAGGCAGAA GGAGGCNGCT TGTTTCANGG TTTGTTCCAA ACACCGTTTN | 60 |

| TTTTTTCAGG GGCCCTTGGT TCCCCAAGAA AGAGANGAAA TCAGTTGTGA GGGCCNNTTT | 120 |

| NTGGTTTTTT TNGTTCAGGG ACNTTTTCAG TGGGCTACTG AGAGAGAGCC AAAGAGCGGC | 180 |

| AGGGAGCTGG AGAAGAGAAT GGCTGAGGTA GAAGCCCAGA AAGCCCAGCA GTTGGAGGAG | 240 |

| GCCAGACTAC AGGAGGAAGA GCAGAAAAAA GAGGAGNTGG CCAGGCTACG GAGAGAACTG | 300 |

| GTGCATAAGG CAAATCCAAT ACGCAAGTAC CAGGGTCTGG AGATAAAGTC AAGTGACCAG | 360 |

-continued

| | | | | | |
|---|---|---|---|---|---|
| CCTCTGACTG | NGCCTGTATC | TCCCCAAATT | CTCCACTCGA | TTCCACTGCT | TAAATTCAGC | 420 |
| TGTGAGCTGC | GGATACCGCC | CGGCAATGGG | ACCTGTTTTT | AACTTCAAAC | CTAGGACCGT | 480 |
| CTTGCTTTGT | CATTGGGCAT | GGAGAGAACC | CATTTNTCCA | GACTTTTACC | TACCCGTGCC | 540 |
| TGAGAAAGCA | TACTTGACAA | CTGTGGACTC | CAGTTTTGTT | GAGAATTGTT | TTCTTACATT | 600 |
| ACTAAGGCTA | ATAATGAGAT | GTAACTCATG | AATGTCTCGA | TTAGACTCCA | TGTAGTTACT | 660 |
| TCCTTTAAAC | CATCAGCCGG | CCTTTTATAT | GGGTCTTCAC | TCTGACTAGA | ATTTAGTCTC | 720 |
| TGTGTCAGCA | CAGTGTAATC | TCTATTGCTA | TTGCCCCTTA | CGACTCTCAC | CCTCTCCCCA | 780 |
| CTTTTTTTAA | AAATTTTAAC | CAGAAAATAA | AGATAGTTAA | ATCCTAAGAT | AGAGATTAAG | 840 |
| TCATGGTTTA | AATGAGGAAC | AATCAGTAAA | TCAGATTCTG | TCCTCTTCTC | TGCATACCGT | 900 |
| GAATTTATAG | TTAAGGATCC | CTTTGCTGTG | AGGGTAGAAA | ACCTCACCAA | CTGCACCAGT | 960 |
| GAGGAAGAAG | ACTGCGTGGA | TTCATGGGGA | GCCTCACAGC | AGCCACGCAG | CAGGCTCTGG | 1020 |
| GTGGGGCTGC | CGTTAAGGCA | CGTTCTTTCC | TTACTGGTGC | TGATAACAAC | AGGGAACCGT | 1080 |
| GCAGTGTGCA | TTTTAAGACC | TGGCCTGGAA | TAAATACGTT | TTGTCTTTCC | CTCCC | 1135 |

ISOLATED NUCLEIC ACID MOLECULES ASSOCIATED WITH GASTRIC CANCER AND METHODS FOR DIAGNOSING AND TREATING GASTRIC CANCER

FIELD OF THE INVENTION

This invention relates to the isolation of genes associated with gastric cancer, methods of diagnosing gastric cancer using these, as well as other genes which are known, as well as therapeutic approaches to treating such conditions.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromography (HPLC). Antigenic peptides are identified after they bind to empty MHC-class I molecules of mutant cell lines, defective in antigen processing, and induce specific reactions with cytolytic T-lymphocytes ("CTLs") These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. Nos. 6,025,191, and 5,698, 396. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has now been applied to stomach cancer samples. Several nucleic acid molecules have been newly isolated and sequenced, and are now associated with stomach cancer. Further, a pattern of expression involving these, as well as previously isolated genes has been found to be associated with stomach cancer. These results are the subject of this application, which is elaborated upon in the disclosure which follows.

DETAILED DESCRIPTION OF PREFERRED EMBODIMENTS

EXAMPLE 1

A stomach cancer cDNA library was established, using standard techniques, then the library was screened, using the SEREX methodology described supra, and set forth by Sahin et al., Proc. Natl. Acad. Sci. USA 92: 11810 (1995), and by Chen et al., Proc. Natl. Acad. Sci. USA 94: 1914 (1997), incorporated by reference in their entirety.

To be specific, total RNA was isolated by homogenizing tumor samples in 4M guanidium thiocyanate/0.5% sodium N-lauryl sarcosine/ and 25 mM EDTA followed by centrifugation in 5.7 M CsCl/25 mM sodium acetate/10 uM EDTA at 320,000 rpm. Total mRNA was removed by passing the sample over an oligo-dT cellulose column. The cDNA libraries were then constructed by taking 5 ug of niRNA, using standard methodologies to reverse transcribe the material.

Libraries were prepared from three different patients, referred to as "SM", "CK" and "SS" respectively. A total of $2.5 \times 10^6$, $1.1 \times 10^6$, and $1.7 \times 10^6$ cDNA clones were obtained from the individuals.

The cDNA was used to construct a lambda phage library, and 500 phages were plated onto XL1-Blue MRF E. coli, and incubated for eight hours at 37° C. A nitrocellulose membrane was then placed on the plate, followed by overnight incubation. The membrane was then washed, four times, without TBS which contained 0.05% Tween, and was then immersed in TBS containing 5% non-fat dried milk. After one hour, the membrane was incubated with conjugates of peroxidase-goat anti human IgG specific for Fc portions of huma antibody (1:2000, diluted in TBS with 1% BSA. The incubation was carried out for one hour, at room temperature, and the membrane was then washed three times with TBS. Those clones which produced antibodies were visualized with 0.06%, 3,3'diamino benzidine tetrachloride, and 0.015% $H_2O_2$, in 50 mM Tris (pH 7.5). Any clones which produced immunoglobulin were marked, and then the membrane was washed, two further times, with TBS that contained 0.05% Tween, and then twice with "neat" TBS.

The membranes were then incubated in 1:100 diluted patient serum, overnight, at 4° C. The patient serum had been pretreated. Specifically, 5 ml samples were diluted to 10 ml with TBS containing 1% bovine serum albumin, and 0.02% $Na_3N$. The serum had been treated to remove antibodies to bacteriophage, by passing it through a 5 ml Sepharose column, to which a lysate of E. coli Y1090 had been attached, followed by passage over a second column which had E. coli lysate and lysate of E. coli infected with lambda bacteriophage. The screening was carried out five time. The samples were then diluted to 50 ml, and kept at −80° C., until used as described herein.

Following the overnight incubation with the membrane, the membrane was washed twice with TBS/0.05% Tween 20, and then once with TBS. A further incubation was carried out, using the protocols discussed supra, for the POD labelled antibodies.

In the case of library SM, 55 positive clones were obtained. Library CK yielded 56 positive clones after the first screening, and after two additional screenings, this number was reduced to 26.

The 55 positive clones were then sequenced, using standard techniques. Following comparison of the sequences to information available in data banks, a total of 36 clones were resolved into known and unknown genes. In the table that follows, the "+" and "−" signs are essentially used to compare signals to each other. All were positive. Table 1, which follows, summarizes some of this work. Specifically, with reference to the first page of the table, previously identified human proteins and the nucleotide sequences, set forth in SEQ ID NOS: 1 to 39 are known. The four molecules which follow (gelsolin, zinc finger protein family, variant zinc finger motif protein goliath and homeodomain proteins, have not been identified in humans previously, although there are related molecules found in other species. SEQ ID NOS: 40 and 47 set forth these nucleotides sequences. Finally, with reference to the table the last four moieties, i.e., prepro-α collagen, heterogeneous ribonucleoprotein D, nucleosome assembly protein 2, and NY-ESO-2/Ulsn NRP/V1 small nuclear ribonucleoprotein, are also known. Nucleotide sequences are set forth at SEQ ID NOS: 48 to 55. The nucleic acid molecules having the nucleotide sequences set forth at SEQ ID NOS: 56 to 83 represent molecules for which no related sequences were found. SEQ ID NO: 84 combines the sequences of SEQ ID NOS: 40 to 43, inclusive. SEQ ID NO: 85 combines SEQ ID NOS: 56–69, SEQ ID NO: 86 combines SEQ ID NOS: 70, 72 and 75, while SEQ ID NO: 87 combines SEQ ID NOS: 71, 73, 74 and 76.

| | Clone | Reactivity | Insert size |
|---|---|---|---|
| RPB-Jx/ | S366 | ++ | 1.75 |
| Human H-2K | S224 | ++ | 1.56 |
| Binding Factor 2 | S541 | ++ | 1.98 |
| (7 clones) | S584 | ++ | 1.86 |
| | S194 | ++−+ | 2.43 |
| | S344 | + | 1.69 |
| | S699 | + | 1.85 |
| Telomeric Repeat | S385 | ++ | 0.96 |
| Binding Protein | S4510 | ++ | 0.96 |
| (2 clones) | | | |
| Protein Kinase B/ | S621 | ++ | 2.00 |
| AKT/Serine- | S641 | + | 1.80 |
| Threonine Protein | | | |
| Kinase rac alpha | | | |
| (2 clones) | | | |
| SRY Interacting | S72 | ++ | 1.70 |
| Protein-1/ | S321 | ++ | 1.76 |
| Tyrosine Kinase | | | |
| Activator Protein | | | |
| (2 clones) | | | |
| Sterol Carrier | S571 | ++ | 2.20 |
| Protein-X/Sterol | S613 | ++ | 2.25 |
| Carrier Protein-2 | S62 | + | 2.91 |
| (3 clones) | | | |
| Archain/ | S537 | ++ | 3.42 |
| Coat Protein Delta- | S632 | ++ | 0.90 |
| Cop (Bovine) | S591 | ++−+ | 3.50 |
| (3 clones) | | | |
| HEM-1 | S551 | ++ | 1.95 |
| (2 clone) | S634 | ++ | 3.46 |
| Id-1 | S271 | +++ | 1.21 |
| Helix-Loop-Helix | | | |
| Protein | | | |
| (1 clone) | | | |
| E2A | S231 | ++ | 1.66 |
| Helix-Loop-Helix | | | |
| Transcription | | | |
| Factor | | | |
| (1 clone) | | | |
| Follistatin-Related | S706 | + | 3.60 |
| Protein | | | |
| (1 clone) | | | |
| Translation | S274 | + | 3.82 |
| Initiation Factor | | | |
| eIF-4γ | | | |
| (1 clone) | | | |
| M Phase | S204 | + | 4.71 |
| Phosphoprotein 1 | | | |
| (1 clone) | | | |
| Lysyl tRNA | S691 | + | 1.80 |
| Synthetase | | | |
| (1 clone) | | | |
| Gelsolin Family | S564 | ++ | 2.04 |
| (2 clone) | S26 | + | 2.57 |
| Zinc Finger | S343 | ++−+ | 0.90 |
| Protein Family | | | |
| (1 clone) | | | |
| A Variant Zinc- | S622 | ++−+ | 1.70 |
| Finger-Motif Protein | | | |
| Goliath | | | |
| Homeodomain | S4611 | + | 3.20 |
| Protein Family | | | |
| (1 clone) | | | |
| Prepro-α1(1) | S563 | ++ | 3.28 |
| Collagen | | | |
| (1 clone) | | | |
| Heterogeneous | S292 | + | 1.25 |
| Ribonucleaprotein D | S222 | + | 2.49 |
| (3 clones) | S232 | + | 1.60 |
| Nucleosome | S524 | + | 1.52 |
| Assembly Protein 2 | | | |
| (1 clone) | | | |
| NY-ESO-2/ | S623 | + | 0.9 |
| Ulsn NRP | | | |
| U1 Small Nuclear | | | |
| Ribonucleoprotein | | | |
| (1 clone) | | | |

The foregoing examples demonstrate several features of the invention. These include diagnostic methods for determining presence of transformed cells, such as gastric cancer cells, in a sample. The sample may contain whole cells or it may be, e.g., a body fluid sample, or an effusion, etc., where the sample may contain cells, but generally will contain shed antigen. The experiments indicate that there is a family of proteins, expression of which is associated with gastric cancer. Hence, the invention involves, inter alia, detecting at least two of the proteins set out in Table 1 wherein, presence of these is indicative of a pathology, such as gastric cancer or other type of related condition. Exemplary of the type of diagnostic assays which can be carried out are immunoassays, amplification assays (e.g., PCR), or, what will be referred to herein as a "display array". "Display array" as used herein refers to a depiction of the protein profile of a given sample. Exemplary of such displays are 2-dimensional electrophoresis, banding patterns such as SDS-gels, and so forth. Thus, one aspect of the invention involves diagnosing gastric cancer or a related condition by determining protein display of a sample, wherein a determination of at least two of the proteins, or expression of their genes, as set forth in Table 1, is indicative of gastric cancer or a related condition. There are many ways to carry out these assays. For example, as indicated herein, antibodies to the proteins were found in patient samples. One can assay for these antibodies using, e.g., the methodology described herein, or by using a purified protein or proteins or antigenic fragment thereof, and so forth. One can also assay for the protein itself, using antibodies, which may be isolated from samples, or generated using the protein and standard techniques. This antibodies can then be labelled, if desired, and used in standard immunoassays. These antibodies or oligonucleotide probes/primers may also be used to examine biopsied tissue samples, e.g., to diagnose precancerous conditions, early stage cancers, and so forth.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. One can monitor the course of an abnormality such as gastric cancer which involve expression of any one of the proteins, the expression of which is governed by nucleic acid molecules which comprise SEQ ID NOS: 40–47 and 56–87, simply by monitoring levels of the protein, its expression, and so forth using any or all of the methods set forth supra.

As has been indicated supra, the isolated nucleic acid molecules which comprise the nucleotide sequences set forth in SEQ ID NOS: 40–47 and 56–87 are new, in that they have never been isolated before. These nucleic acid molecules may be used as a source to generate gastric cancer specific proteins and peptides derived therefrom, and oligonucleotide probes which can themselves be used to detect expression of these genes. Hence, a further aspect of the invention is an isolated nucleic acid molecule which comprises any of the nucleotide sequences set forth in SEQ ID NOS: 40–47 and 56–87, or molecules whose complements hybridize to one or more of these nucleotide sequences, under stringent conditions, expression vectors comprising these molecules, operatively linked to promoters, cell lines and strains transformed or transfected with these, and so forth. "Stringent conditions", is used herein, refers to condition such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

It should be clear that these methodologies may also be used to track the efficacy of a therapeutic regime. Essentially, one can take a baseline value for the protein or proteins being tested, using any of the assays discussed supra, administer a given therapeutic, and then monitor levels of the protein or proteins thereafter, observing changes in protein levels as indicia of the efficacy of the regime.

For those proteins which have been identified previously, i.e., those in Table 1, similar assays can be carried out, but for two or more of the proteins or nucleic acid molecules encoding them. Specifically, telomeric repeat binding protein, or protein kinase B/AKT/serine threonine protein kinase rac alpha are preferably determined, either in the form of the protein per se, or nucleic acid molecules encoding them (e.g., SEQ ID NOS: 10–14), together, or in combination with one or more of human gelsolin (SEQ ID NOS: 40–43 and 84), one or more of SEQ ID NOS: 56–76, 85, 86 or 87), or the proteins encoded by these sequences, and so forth The identification of the proteins set forth herein as being implicated in pathological conditions such as gastric cancer also suggests a number of therapeutic approaches to such conditions. The experiments set forth supra establish that antibodies are produced in response to expression of these proteins, suggesting their use as a vaccine. Hence, a further embodiment of the invention is the treatment of conditions which are characterized by expression of one or more of the subject proteins, via immunotherapeutic approaches. One of these approaches is the administration of an amount of one or more these proteins, or an immunogenic peptide derived therefrom in an amount sufficient to provoke or augment an immune response. The proteins or peptides may be combined with one or more of the known immune adjuvants, such as saponins GM-CSF interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the protein or proteins. These antibodies may be, e.g., antibodies produced via any of the standard approaches elaborated upon supra.

T cell responses may also be elicited by using peptides derived from the proteins which then complex, non-covalently, with MHC molecules, thereby stimulating proliferation of cytolytic T cells against any such complexes in the subject. It is to be noted that the T cells may also be elicited in vitro, and then reperfused into the subject being treated.

Note that the generation of T cells and/or antibodies can also be accomplished by administering cells, preferably treated to be rendered non-proliferative, which present relevant T cell or B cell epitopes for response.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptides expressing sequences in all possible variations, such as one from each protein, several from one or more protein and one from each of the additional proteins, a plurality from some and none from others, and so forth.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. An isolated nucleic acid molecule selected from the group consisting of:
   (a) nucleic acid molecules which encode a gastric cancer associated antigen, and which consist of a nucleotide sequence selected from the group consisting of the nucleotide sequences set forth as SEQ ID NOS:56–66, 68, 69 and 85, and
   (b) full length complements of (a).

2. A vector comprising an insert consisting of the isolated nucleic acid molecule of claim 1, operably linked to a promoter.

3. A cell line or cell strain, transformed or transfected with the expression vector of claim 2.

4. A composition of matter, comprising the vector of claim 2, and a pharmaceutically acceptable carrier.

5. A cell line or cell strain, transformed or transfected with the isolated nucleic acid molecule of claim 1.

6. A composition of matter, comprising a therapeutically effective amount for treating gastric cancer of the cell line or cell strain of claim 5, and having presented on its surface, a peptide encoded by the isolated nucleic acid molecule complexed to an MHC molecule to form a complex which provokes an immune response against stomach cancer cells.

7. The isolated nucleic acid molecule of claim 1, which consists of at least one of the nucleotide sequences set forth as SEQ ID NOS:56–66, 68, and 69.

8. The isolated nucleic acid molecule of claim 1, which consists of the nucleotide sequence set forth as SEQ ID NO: 85.

9. A composition of matter, comprising the isolated nucleic acid molecule of claim 1, and a pharmaceutically acceptable carrier.

10. The nucleic acid molecule of claim 1, wherein the nucleic acid molecule codes for an immunogenic polypeptide.

11. An vector comprising an insert consisting of the isolated nucleic acid molecule of claim 10, operably linked to a promoter.

12. A cell line or cell strain, transformed or transfected with the isolated nucleic acid molecule of claim 10.

13. An isolated cell line or cell strain, transformed or transfected with the vector of claim 11.

14. An isolated antisense molecule which binds to the nucleic acid molecule of claim 1.

15. The isolated antisense molecule of claim 14, wherein the antisense molecule is a DNA molecule.

16. The isolated antisense molecule of claim 14, wherein the antisense molecule is from 10 to 100 nucleotides in length.

17. An expression vector comprising the isolated antisense molecule of claim 14, operably linked to a promoter.

18. A cell line or cell strain, transformed or transfected with the isolated antisense molecule of claim 14.

19. A cell line or cell strain, transformed or transfected with the expression vector of claim 17.

* * * * *